(12) United States Patent
Mizumoto et al.

(10) Patent No.: US 7,815,947 B2
(45) Date of Patent: *Oct. 19, 2010

(54) NUTRITIONAL COMPOSITION FOR CONTROLLING BLOOD SUGAR LEVEL

(75) Inventors: Kenji Mizumoto, Odawara (JP); Hajime Sasaki, Odawara (JP); Hisae Kume, Odawara (JP); Makoto Yamaguchi, Odawara (JP)

(73) Assignee: Meiji Dairies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/275,296

(22) Filed: Nov. 21, 2008

(65) Prior Publication Data

US 2009/0143277 A1 Jun. 4, 2009

Related U.S. Application Data

(63) Continuation of application No. 10/487,237, filed as application No. PCT/JP02/09092 on Sep. 6, 2002.

(30) Foreign Application Priority Data

| Sep. 7, 2001 | (JP) | ............................. 2001-272463 |
| Mar. 15, 2002 | (JP) | ............................. 2002-73141 |
| Mar. 15, 2002 | (JP) | ............................. 2002-073141 |
| May 31, 2002 | (JP) | ............................. 2002-160602 |

(51) Int. Cl.
*A61K 36/48* (2006.01)
*A23C 9/00* (2006.01)

(52) U.S. Cl. ........................................ 424/757; 426/34

(58) Field of Classification Search ........................ None
See application file for complete search history.

(56) References Cited

U.S. PATENT DOCUMENTS

| 5,166,189 A | 11/1992 | Trimbo et al. |
| 5,198,250 A | 3/1993 | Brillhart et al. |
| 5,256,640 A | 10/1993 | Peterson et al. |
| 5,605,893 A | 2/1997 | Kaufman |
| 5,714,472 A | 2/1998 | Gray et al. |
| 5,776,887 A * | 7/1998 | Wibert et al. .................. 514/2 |
| 5,843,921 A | 12/1998 | Kaufman |
| 6,156,738 A | 12/2000 | Bell et al. |
| 6,207,638 B1 | 3/2001 | Portman |
| 6,248,375 B1 | 6/2001 | Gilles et al. |
| 6,303,353 B1 * | 10/2001 | Sugiyama et al. ........... 435/158 |
| 2002/0018812 A1 | 2/2002 | Busson et al. |

FOREIGN PATENT DOCUMENTS

| EP | 0 648 495 | 4/1995 |
| EP | 0 794 259 | 9/1997 |
| EP | 0 898 900 | 3/1999 |
| JP | 52-15834 | 2/1977 |
| JP | 63-112963 | 5/1988 |
| JP | 11-18725 | 1/1999 |
| JP | 2001-103928 | 4/2001 |
| JP | 2001-128642 | 5/2001 |
| WO | 93/22271 | 11/1993 |
| WO | 01/33976 | 5/2001 |
| WO | 02/11562 | 2/2002 |

OTHER PUBLICATIONS

Kawai et al. Usefulness of Palatinose As a Caloric Sweetener for Diabetic Patients. Horm. Metabol. Res. 21. 338-340. 1989.*
Hotamisligil et al. Increased Adipose Tissue Expression of Tumor Necrosis Factor Alpha in Human Obesity and Insulin Resistance. J. Clin Invest. vol. 95. pp. 2409-2415. 1995.*
K. Kawai, et al., "Usefulness of Palatinose as a Caloric Sweetener for Diabetic Patients", Hormone and Metabolic Research, vol. 21, No. 6, pp. 338-340 (1989).
Y. Okuda, et al., "Effects of Parenteral Palatinose on Glucose Metabolism in Normal and Streptozotocin Diabetic Rats", Hormone and Metabolic Research, vol. 18, No. 6, pp. 361-364 (1986).
K. Kawai, et al., "Changes in Blood Glucose and Insulin after an Oral Palatinose Administration in Normal Subjects", Endocrinologia Japonica, vol. 32, No. 6, pp. 933-936 (1985).
S. Aoyagi, Food Style 21, vol. 3, No. 1, pp. 54-57, with partial English translation (1991).
H. Arima, Food Style 21, vol. 3, No. 1, pp. 58-62, with partial English translation (1991).
S. Inoue, et al., Food Style 21, vol. 6, No. 5, pp. 46-52, with partial English translation (2002).
Kiso To Rinsho, vol. 29, No. 17, pp. 4529-4543, with English abstract (1995).
Palou, et al., "Obesity: molecular bases of a multifactorial problem", Eur. J. Nutr., vol. 39, pp. 127-144 (2000).
Hotamisligil, et al., "Increased adipose tissue expression of tumor necrosis factor alpha in human obesity and insulin resistance", J. Clin. Invest., vol. 95, pp. 2409-2415 (1995).

* cited by examiner

*Primary Examiner*—Christopher R Tate
*Assistant Examiner*—Melenie McCormick
(74) *Attorney, Agent, or Firm*—Oblon, Spivak, McClelland, Maier & Neustadt, L.L.P.

(57) ABSTRACT

A nutritional composition for controlling blood sugar level comprising a protein, a lipid and a carbohydrate, wherein energy percentages supplied by the protein, lipid and carbohydrate are 10 to 25%, 20 to 35% and 40 to 60%, respectively; and oleic acid in the lipid energy percentage is 60 to 90% and palatinose and/or trehalulose in the carbohydrate energy percentage is 60 to 100%, which is useful as an oral or tube feeding nutrient for nutritional management or blood sugar level control of patients suffering from diabetes and glucose intolerance, or for obesity prevention, a therapeutic diet, a diet for diabetic patients at home, an obesity preventive diet or a food with health claims.

14 Claims, 14 Drawing Sheets

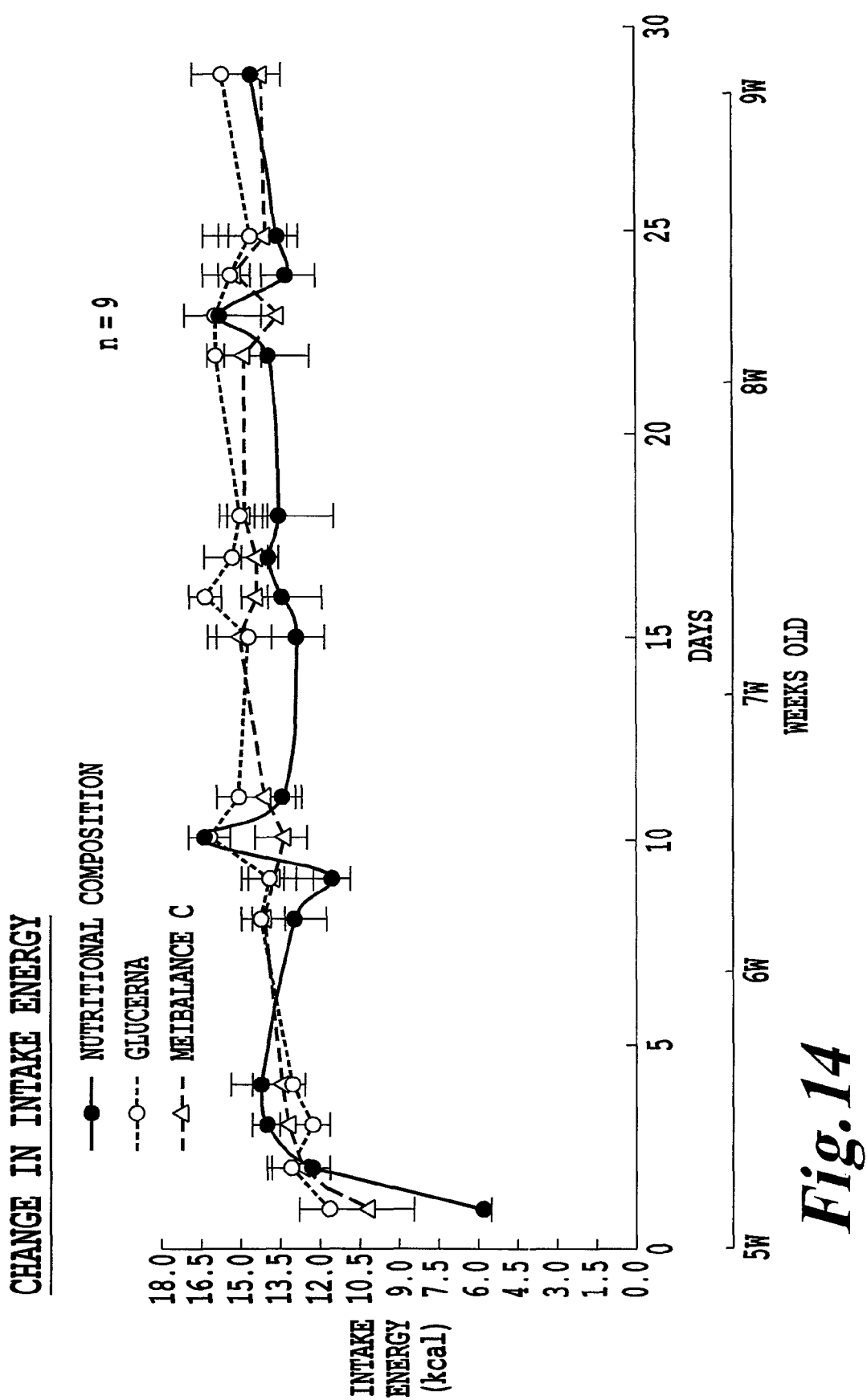

NUTRITIONAL COMPOSITION FOR CONTROLLING BLOOD SUGAR LEVEL

This is a continuation application of U.S. application Ser. No. 10/487,237, filed Feb. 27, 2004, which is a 371 of PCT/JP02/09092 filed on Sep. 6, 2002.

TECHNICAL FIELD

The present invention relates to nutritional compositions for diabetic patients or sufferers having abnormal glucose intolerance, or for preventing obesity.

BACKGROUND ART

In recent years, the number of diabetic patients is increasing with the westernization of eating habits. It is estimated that the number, including potential patients, amounts to 15 million. In the treatment of diabetes, diet therapy and exercise are essential. The objects of these therapies are represented mainly by the maximized normalization of dysbolism of the patients, correction of insulin hyposecretion or insulin resistance which is a factor for causing diabetes, or prevention or inhibition of the advance of vascular complications. Obesity is said to be a prime cause responsible for sixty to eighty percent of diabetes cases. Because excessive insulin secretion is common to most obesity sufferers, there is the possibility that when obesity exceeds a certain level, the secreted amount of insulin becomes too high, leading to deteriorating obesity [Food Style 21, pp. 46, 2002.5 (Vol. 6 No. 5)].

In the U.S.A., with the progress of clinical nutrition science, a variety of oral or tube feeding (enteral) nutritional supplements were developed for various morbidities from the latter half of 1980s to the early 1990s. Examples include "Glucerna" for diabetic patients, "Suplena" for patients with renal disorders who are not receiving artificial dialysis, "Nepro" for patients with renal disorders who require artificial dialysis, "Perative" for all patients during an invasive period, "AlitraQ" for patients during an invasive period, particularly, with impaired digestive tracts, and "Advera" for people with AIDS. In recent years, "OXEPA" for patients with acute respiratory distress syndrome (ARDS) was put on the market. These products account for more than 70% of oral or tube feeding nutritional supplements for morbidities in the U.S.A. [FOOD Style 21, pp 54, 1991.1 (Vol. 3 No. 1)]. In Japan, on the other hand, "YH-80" is a thick fluid diet developed for severe burn patients, "Fibrene YH" having a composition closer to a typical diet than YH80, "Renalene" for patients having diminished renal function, "Meibalance C" which is a total nutrition fluid diet designed for the aged [FOOD Style 21, pp. 58, 1991.1 (Vol. 3 No. 1)], and liquid high-nutrition fluid diet A-3 for unconscious patients [ISO TO RINSHO 29 (17): 4529-4543, 1995] are on the market. Nonetheless, a fluid diet for diabetic patients, such as "Glucerna", is still not on the market.

A number of patents and patent applications related to fluid diets existent, but the number which relate to diabetes remains few. The only recognized so far is a nutritional composition for diabetic patients which contains protein, lipid and carbohydrate at a predetermined energy percentage and which is added with a viscous soluble food fiber and insulin or hydrolyzate thereof (Japanese Patent Laid-Open No. Hei 11-18725).

An object of the present invention is therefore to provide a nutritional composition effective for nutrition management and blood sugar level control of patients suffering from abnormal glucose metabolism, or for obesity prevention. More specifically, the object of the invention is to provide a nutritional composition for diabetic patients or people having abnormal glucose intolerance, or for prevention of obesity, which composition is effective for suppressing a steep rise in the postprandial blood sugar level due to low insulin secretion and insulin resistance and for improving glycohemoglobin (HbA1c) levels which reflects blood sugar levels over a long period of time.

DISCLOSURE OF THE INVENTION

Palatinose is a heterodisaccharide in which glucose and fructose form an α-1,6 bond. Like sucrose, this is digested and absorbed as glucose and fructose [Toshinao Aida, et al.: Journal of Japanese Society of Nutrition and Food Science, Vol. 36(3), 169-173, 1983]. Because the hydrolysis rate of palatinose is one fifth of that of sucrose [Tsuji Y. et al.: J. Nutr. Sci. Vitaminol., 32, 93-100, 1986], blood glucose and insulin levels after intake of palatinose can be maintained at predetermined levels over many hours [Kawai, K. et al.: Endocrinol, Japan, 32(6), 933-936, 1985].

Trehalulose is a hetero disaccharide in which glucose and fructose form an α-1,1 bond. This substance is a digestive, non-carious sweetener having physiological properties similar to those of palatinose. Like palatinose, this substance is digested and absorbed as glucose and fructose by isomaltase in the small intestine. The hydrolysis rate of trehalulose in the small intestine is one third of that of sucrose and about 2 times as much as that of palatinose [Yamada K., Shinohara H. et al.: Nutrition Reports International, 32(5), 1211-1219, 1985].

The Ministry of Health and Welfare (Ministry of Health, Labor and Welfare) has recommended a change to the recommended intake ratio of saturated fatty acids (SFA:palmitic acid, stearic acid and the like): monovalent unsaturated fatty acids (MUFA:oleic acid and the like): polyvalent unsaturated fatty acids (PUFA:linoleic acid, linolenic acid and the like) from 1:1.5:1 to 3:4:3 and to adjust the ratio of n-6 series fatty acids:n-3 series fatty acids to 4:1. The above-described change has been made because in Japan, it is difficult to consume a diet containing a ratio of MUFA of as much as 1.5.

The present inventors therefore prepared a nutritious composition containing protein, lipid and carbohydrate at a specific energy percentage and studied its effect on fasting blood sugar levels of normal animals. As a result, the nutritional composition showed similar inhibition of increase in blood sugar levels as that of Glucerna, a commercial fluid diet for diabetic patients. As a result of the study on the blood-sugar-level rise inhibition and the morbid condition alleviating effect of this nutritional composition using experimental diabetic model animals and spontaneous diabetic model animals, it exhibited a similar inhibition of increase in blood sugar levels as that of Glucerna and at the same time, showed a significant lipid metabolism improving action relative to Glucerna. When a single oral administration test of this nutritional composition was conducted using normal healthy subjects, insulin after administration remained at low levels. Moreover, its effects on visceral fat accumulation of normal animals were studied, showing superior inhibition of visceral fat accumulation to Glucerna and Meibalance C. It has been found, from the above-described results, that this nutritious composition is effective for controlling the blood sugar level of patients suffering from diabetes or glucose intolerance, or for obesity prevention, leading to the completion of the present invention.

In the present invention, there is thus provided a nutritional composition for blood sugar level control which contains a protein, a lipid and a carbohydrate, wherein energy percentages supplied by the protein, lipid and carbohydrate are 10 to 25%, 20 to 35% and 40 to 60%, respectively; and a percentage of oleic acid in the lipid energy ratio is 60 to 90% and the percentage of palatinose and/or trehalulose in the carbohydrate energy ratio is 60 to 100%.

In the present invention, there is also provided use of a composition which contains a protein, a lipid and a carbohydrate, wherein energy percentages supplied by the protein, lipid and carbohydrate are 10 to 25%, 20 to 35% and 40 to 60%, respectively; and a percentage of oleic acid in the lipid energy ratio is 60 to 90% and the percentage of palatinose and/or trehalulose in the carbohydrate energy ratio is 60 to 100% for the preparation of a nutritional composition for controlling blood sugar level and preventing obesity.

In the present invention, there is further provided a method for controlling the blood sugar level and preventing obesity, which is characterized by administering to a subject a nutritional composition for blood sugar level control which contains a protein, a lipid and a carbohydrate, wherein energy percentages supplied by the protein, lipid and carbohydrate are 10 to 25%, 20 to 35% and 40 to 60%, respectively; and a percentage of oleic acid in the lipid energy ratio is 60 to 90% and the percentage of palatinose and/or trehalulose in the carbohydrate energy ratio is 60 to 100%.

BRIEF DESCRIPTION OF THE DRAWINGS

FIG. 14 is a graph showing a change in the intake energy of C57BL/6N Jcl mice after they were fed ad libitum with each of the nutritional composition, Glucerna and Meibalance C powder for 1 month. In the diagram, (●) means the nutritional compositions, (○) means Glucerna and (△) means Meibalance C. Each point is a mean value±standard deviation (n=9). *: P<0.05: (Mann-Whitney U-test).

BEST MODE FOR CARRYING OUT THE INVENTION

Figure 1:
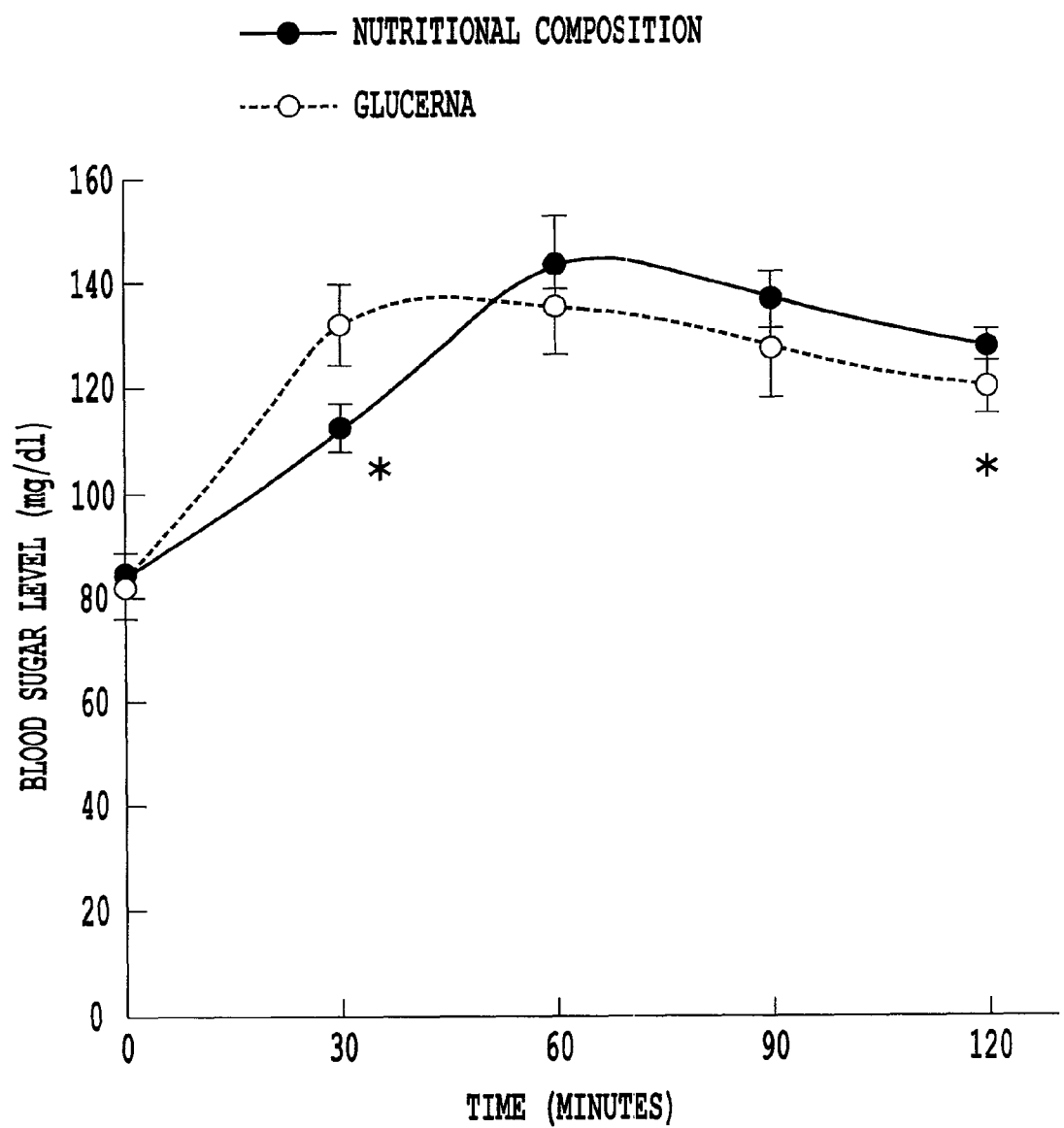
FIG. 1 is a graph showing change in the blood sugar level after oral administration of each of the nutritional composition and Glucerna to normal rats. In the diagram, (-●-) means the nutritional composition, while (••○••) means Glucerna. Each point is a mean±standard deviation (n=6). *: P<0.05: Significant difference from Glucerna (Student-t Test).

The nutritional composition of the present invention (which will hereinafter be called "the nutritional composition" or "the composition") contains a protein at an energy percentage of 10 to 25%, preferably 10 to 20% in the composition.

Examples of the protein include milk proteins, plant-derived proteins and soybean protein or hydrolyzate thereof. Among them, the milk proteins are preferred. Examples of the milk proteins include MPC (Milk Protein Concentrate), casein protein, whey proteins, and magnesium caseinate, and hydrolyzate thereof, and fermented milk and a component obtained by removing whey from the fermented milk (fresh cheese, quark, etc.) (Japanese Patent Laid-Open No. Hei 5-252896). Among them, MPC and a combination of MPC and casein are most preferred.

Examples of the whey proteins include whey powder obtained by concentrating and drying whey, whey protein concentrate (WPC) obtained by concentrating whey by ultrafiltration (UF) and then drying, defatted WPC (low fat and high protein content) obtained by removing fat from whey, followed by UF concentration, WPI obtained by selectively isolating only protein from whey, desalted whey obtained by nanofiltration concentration, and mineral concentrated whey in which mineral components derived from whey have been concentrated.

The nutritional composition of the present invention contains a lipid at an energy percentage of 20 to 35%, preferably 20 to 30% in the composition. This ratio is in accordance with the Recommended Dietary Allowances for the Japanese, 6th Revision. To heighten the content of monovalent unsaturated fatty acids (MUFA) in the fatty acid composition in the lipid, oleic acid, which is a monovalent unsaturated fatty acid, is incorporated in the lipid at an energy percentage of 60 to 90%, preferably 60 to 80%. Examples of the lipid source rich in oleic acid include high oleic sunflower oil, rapeseed oil, olive oil, high-oleic-acid safflower oil, soybean oil, corn oil and palm oil, each having a high oleic acid content. The lipid source abundant in oleic acid is, for example, Nutrition Controlled Oil or Fat (product of NOF). Sunflower oil, rapeseed oil, olive oil and a mixture with an olive oil are also usable.

As another lipid, phospholipid derived from milk or lecithin (derived from soybean or yolk) is preferred.

Milk phospholipid exists only in a milk fat globule membrane (FFGM). Examples of milk phospholipid containing much MFGM include lyophilizate of byproduct (MF retentate) of WPI prepared using ultrafiltration (UF) and microfiltration (MF) in combination, and a fraction (butter serum) obtained by removing butter oil from whey cream. A lipid fraction obtained by extracting butter serum with ethanol several times, followed by concentration, or an acetone insoluble fraction (α-Lipid: product of Anchor Products/New Zealand) is also usable.

Lecithin chemically means phosphatidylcholine (PC), however, it usually refers to a mixture of 4 compounds, that is, PC, phosphatidyl ethanolamine (PE), phosphatidyl inositol (PI) and phosphatidic acid (PE), and another phospholipid. In the present invention, these lecithins are all usable. In addition, lecithin paste having an acetone insoluble fraction, serving as an indicator of phospholipid purity, of from 62 to 65%, high-purity powdery lecithin having a phospholipid content of 95% or greater, and a fractionated lecithin having an increased phosphatidyl choline content.

The composition of the present invention may contain n-6 series polyvalent unsaturated fatty acids and n-3 series polyvalent unsaturated fatty acids. Preferably, these polyvalent unsaturated fatty acids amount to 10 to 40%, preferably 10 to 30% of the fatty acid composition. For example, these polyvalent unsaturated fatty acids can be incorporated in an amount of about 20% in the fatty acid composition.

With regards to the lipid composition of the nutritional composition, the n-6 series polyvalent unsaturated fatty acids and the n-3 series polyvalent unsaturated fatty acids can be incorporated at a ratio of from about 5:1 to about 1:1, preferably about 4:1. To attain this ratio, incorporation of perilla oil or linseed oil, which contains n-3 series α-linolenic acid at a high ratio is recommended. Bonito or tuna oil rich in DHA is also usable.

In the present invention, at least one selected from milk phospholipid, soybean lecithin, high oleic sunflower oil and perilla oil is preferably used as the lipid.

In the nutritional composition of the present invention, the carbohydrate is incorporated at an energy percentage of from 40 to 60%, preferably from 50 to 60%. This energy percentage approximately corresponds to the Recommended Dietary Allowances for the Japanese, 6th Revision. As the carbohydrate, palatinose, trehalulose or mixture thereof is used. Palatinose, trehalulose or mixture thereof is incorporated in the carbohydrate at an energy percentage of 60 to 100%, preferably 60 to 80%.

Examples of another carbohydrate include sugar alcohols (sorbitol, xylitol and maltitol), trehalose, palatinit, maltodextrin, processed starch, amylose starch, tapioca starch, fructose and lactose, and mixture thereof. Of these, maltodextrin, xylitol and mixture thereof are preferred. Maltodextrin is a sugar which is an intermediate product available by acid hydrolysis or enzymolysis of starch or corn starch and its DE value of 20 or less.

The nutritional composition of the present invention may further contain food fiber. The food fiber may either be water soluble food fiber or non-water-soluble food fiber. Examples of the water soluble food fiber include sparingly digestible dextrin, pectin, glucomannan, alginic acid, hydrolyzate of alginic acid, guar gum, product of guar gum obtained by enzymolysis, and galactomannan. Sparingly digestible dextrin is preferred because it can be easily added to food and does not disturb food processing. Examples of the non-water-soluble food fiber include crystalline cellulose, soybean food fiber, wheat bran, corn fiber and beat fiber.

The nutritional composition of the present invention may contain vitamins and minerals in amounts according to a standard fluid diet. Vitamins include Vitamin $B_2$, nicotinic amide, Vitamin $B_6$, calcium pantothenate, folic acid, Vitamin $B_{12}$, Vitamin A fatty acid ester, Vitamin $D_3$, α-vitamin E, Vitamin $K_2$, sodium L-ascorbate and β-carotene. Minerals include calcium, phosphorous, iron, sodium, potassium, chlorine and magnesium and naturally occurring trace elements, for example, yeast minerals such as copper, zinc, selenium, manganese and chromium. Copper gluconate and zinc gluconate are also usable.

The nutritional composition of the present invention has an osmotic pressure of about from 300 to 1000 mOsm/L, for example, from about 300 to 750 mOsm/L. The viscosity of the nutritional composition, when measured at room temperature, is preferably from about 5 to 40 mPa·s, especially from 5 to 20 mPa·s.

The nutritional composition preferably has a calorie content of from about 0.7 to 3 kcal/mL, especially from 1 to 1.5 kcal/mL.

The nutritional composition in the directly usable form is preferred. The composition in this form can be administered via tube from nose—stomach and then jejunum or orally. Such a nutritional composition may take various forms such as fruit juice type beverage or milk shake type beverage. The nutritional composition may be soluble powder which can be reconstituted before use.

The nutritional composition may contain various flavors (ex. vanilla), sweeteners and other additives. As the artificial sweetener, aspartame or the like is usable.

Champignon extract having feces odor reducing effect can be added in an amount of from 5 to 500 mg (0.005 to 0.5%) and carotenoid preparations (for example, α-carotene, β-carotene, lycopene and lutein) can be added in an amount of from 10 to 200 μg (0.00001 to 0.0002%) for nutrition reinforcement.

As an antioxidant, catechin or polyphenol may be added.

The nutritional composition can be prepared, for example, by mixing the protein, the lipid and the carbohydrate at the above-described mixing ratio. In this case, an emulsifier can be added to the mixture.

The nutritional composition of the present invention can be obtained as a product in a manner known per se in the art, for example, by sterilizing a liquid nutritional composition by heating in advance and then antiseptically filling a container therewith (ex. use of UHT sterilization and aseptic package method), or by filling a container with a liquid nutritional composition and then sterilizing the composition together with the container by heating (ex. autoclave method).

Use of the product as a liquid is intended, a homogenized composition is filled in a can container, followed by retort sterilization; or is sterilized under heating at about 140 to 145° C. for about 5 to 8 seconds again, cooled and then aseptically filled in a container. For the use of the product as powder, the homogenized composition is, for example, spray dried. For the use as a solid, agar or the like is added to solidify the composition.

The nutritional composition of the present invention is effective for nutrition management and blood sugar level control of patients suffering from diabetes or abnormal glucose metabolism, and for obesity prevention. More specifically, it is useful for nutrition management of patients suffering from type I diabetes, type II diabetes, glucose intolerance, postoperative glucose tolerance disorders and impaired glucose tolerance. It is also usable for controlling their blood sugar level. The nutritional composition is also useful for patients having a risk of recurrence of hyper glycemia or as a supplement for diet therapy of diabetic patients. It is also effective for the prevention of obesity which will otherwise become a risk factor inducing diabetes.

In the neurosurgical field, there are many patients who have consciousness disorders and cannot eat voluntarily. If such patients are 40 years old or more, they tend to suffer some complications. To these patients having consciousness disorders, nutrients can be administered through the intestinal tract, which is a more physiological pathway for taking a diet, because their digestive absorbing capacity tends to be free from damage. The nutritional composition of the present invention therefore plays an important role in nutrition management. In patients of multi organ disorders (MODS) who also suffer from renal failure, abnormalities in water-electrolyte tend to occur, leading to a hindrance to enteral nutrition from an early stage. There is accordingly a demand for a liquid nutritional composition designed while paying attention to water-electrolyte in renal failure. The nutritional composition of the present invention can be expected also as such a composition.

It has been pointed out that in not only diabetic patients but also healthy people, a drastic increase in blood sugar level and insulin secretion after meals promotes accumulation of visceral fat, which presumably induces onset of life-style related diseases such as hyperlipemia, hypertension and arteriosclerosis. Accordingly, preparation of meals in consideration of the postprandial blood sugar level control is fundamental for the diet therapy of diabetes and it is also important for prevention of life-style related diseases. The nutritional composition of the present invention can be used as, as well as oral or tube-feeding nutrient, therapeutic diet or diet for diabetic patients at home, obesity preventing diet or food with health claims (food for specified health uses and food with nutrient function claims).

Administration of the nutritional composition to patients depends on their state, weight or age, or whether the composition is only one nutrient or not. Its dose is determined by a doctor in charge. When the nutritional composition is used as a supplement for another food, its daily dose is reduced, depending on the amount of the other food.

The nutritional composition of the present invention can be administered multiple times a day, for example, from two to five times adding up for the necessary amount for one day, once a day, or continuously for a necessary term.

It can be administered after solidified by adding agar to a liquid nutritional composition, or by adding water and agar to a powdery nutritional composition and after heat treatment, cooling. A solidified nutritional composition can be taken as a substitute for an ordinary solid diet, because it creates the sensation of fullness after meals.

EXAMPLES

The present invention will hereinafter be described more specifically by Examples and Tests. The present invention is however not limited to or by these Examples.

Example 1

A liquid nutritional composition was prepared in accordance with the amounts of raw materials shown below in Table 1. The resulting composition had a calorie of 100 kca/100 mL and it contained protein, lipid and carbohydrate at an energy percentage of 23.7%, 30.2% and 46.1%, respectively. The energy percentage of oleic acid in the lipid was 70%, while that of palatinose in the carbohydrate was 69%. The composition was used as a nutritional composition in Tests.

Employed were milk protein concentrate (MPC) (product of Fonterra/New Zealand), caseinate of DMV, milk phospholipid (product of New Zealand Dairy Ingredients Limited), sparingly digestible dextrin (product of Matsutani Chemical Industry), high oleic sunflower oil (product of NOF corporation) (oleic acid content: 80%), perilla oil (product of NOF Corporation) (6% palmitic acid, 2% stearic acid, 19% oleic acid, 12% linoleic acid and 60% α-linolenic acid), and palatinose (product of Shin Mitsui Sugar).

TABLE 1

| Component | Raw materials | In 100 g basic mixture |
|---|---|---|
| Protein | Milk protein concentrate (MPC) | 5 g |
| | Caseinate | 1 g |
| Lipid | Nutritiously adjusted oil or fat (containing 10% of perilla oil) | 3.0 g |
| | Milk phospholipid | 0.1 g |
| | Soybean lecithin | 0.3 g |
| Carbohydrate | Palatinose | 8 g |
| | Maltodextrin | 3 g |
| | Xylitol | 0.9 g |
| Food fiber | Sparingly digestible dextrin | 1.6 g |
| General component | Flavor | 0.5 g |
| | Citric acid (for pH regulation) | 0.2 g |
| Vitamin | Vitamin A fatty acid ester | 1.3 mg |
| | Vitamin $D_3$ | 0.005 mg |
| | α-vitamin E (α-TE) | 40 mg |
| | Dibenzoyl thiamine hydrochloride | 4.7 mg |
| | Vitamin $B_2$ | 2.6 mg |
| | Vitamin $B_6$ | 3.7 mg |
| | Vitamin $B_{12}$ | 0.005 mg |
| | Niacin | 29.4 mg |
| | Pantothenic acid | 9.5 mg |
| | Folic acid | 0.49 mg |
| | Vitamin C | 60.6 mg |
| | Vitamin $K_2$ | 0.11 mg |
| | α-Carotene | 0.8 μg |
| | β-Carotene | 4.2 μg |
| | lycopene | 1.4 μg |
| | lutein | 5.59 μg |
| Mineral | Sodium chloride | 100 mg |
| | Potassium hydroxide | 150 mg |
| | Magnesium sulfate heptahydrate | 10 mg |
| | Trisodium citrate dihydrate | 120 mg |
| | Ferrous sulfate | 5 mg |

Example 2

A liquid nutritional composition was prepared in accordance with the amounts of raw materials shown below in Table 2. The resulting composition had a calorie of 100 kca/100 mL and it contained protein, lipid and carbohydrate at an energy percentage of 24%, 30% and 46%, respectively. The energy percentage of oleic acid in the lipid was 70%, while that of palatinose in the carbohydrate was 69%. The composition was used as a nutritional composition in Tests.

TABLE 2

| Component | Raw materials | In 100 g basic mixture |
|---|---|---|
| Protein | Milk protein concentrate (MPC) | 3.5 g |
| | Caseinate | 2.4 g |
| Lipid | High oleic sunflower oil + perilla oil | 2.91 g |
| | Milk phospholipid | 0.1 g |
| | Soybean lecithin | 0.29 g |
| Carbohydrate | Palatinose | 7.01 g |
| | Maltodextrin | 2.45 g |
| | Xylitol | 0.9 g |
| Food fiber | Sparingly digestible dextrin | 1.88 g |
| General component | Flavor | 0.5 g |
| | Champignon extract | 0.05 g |
| | Citric acid (for pH regulation) | 0.13 g |
| Vitamin | Vitamin A | 250 IU |
| | Vitamin D | 30 IU |
| | Vitamin E (α-TE) | 13.1 mg |
| | Vitamin $B_1$ | 0.96 mg |
| | Vitamin $B_2$ | 0.6 mg |
| | Vitamin $B_6$ | 0.4 mg |
| | Vitamin $B_{12}$ | 1.1 μg |
| | Niacin | 1.8 mg |
| | Pantothenic acid | 1.2 mg |
| | Folic acid | 75 μg |
| | Vitamin C | 91 mg |
| | α-Carotene | 0.8 μg |
| | β-Carotene | 4.2 μg |
| | Lycopene | 1.4 μg |
| | Lutein | 5.6 μg |
| Mineral | Sodium chloride | 100 mgt |
| | Ferrous sulfate | 5 mg |
| | Chromium yeast | 2 mg |
| | Zinc yeas | 5 mg |
| | Potassium dihydrogen phosphate | 20 mg |
| | Trisodium citrate dihydrate | 100 mg |
| | Potassium hydroxide | 00 mg |

Example 3

A liquid nutritional composition was prepared in accordance with the amounts of raw materials shown below in Table 3. The resulting composition had a calorie content of 100 kca/100 mL and it contained protein, lipid and carbohydrate at an energy percentage of 22, 30% and 48%. The energy percentage of oleic acid in the lipid was 70%, while that of palatinose in the carbohydrates was 69%. The composition was used as a nutritional composition in Tests.

TABLE 3

| Component | Raw materials | In 100 g basic mixture |
|---|---|---|
| Protein | Milk protein concentrate (MPC) | 3.2 g |
| | Caseinate | 2.4 g |
| Lipid | High oleic sunflower oil + perilla oil | 2.9 g |
| | Milk phospholipid | 0.1 g |
| | Soybean lecithin | 0.29 g |
| Carbohydrate | Palatinose | 8 g |
| | Maltodextrin | 3 g |
| | Xylitol | 0.9 g |
| Food fiber | Sparingly digestible dextrin | 1.5 g |
| General | Flavor | 0.4 g |

TABLE 3-continued

| Component | Raw materials | In 100 g basic mixture | |
|---|---|---|---|
| component | Champignon extract | 0.05 | g |
| Vitamin | Vitamin A | 250 | IU |
| | Vitamin D | 30 | IU |
| | Natural Vitamin E (α-TE) | 8 | mg |
| | Vitamin $B_1$ | 0.6 | mg |
| | Vitamin $B_2$ | 0.5 | mg |
| | Vitamin $B_6$ | 0.3 | mg |
| | Vitamin $B_{12}$ | 0.9 | μg |
| | Niacin | 1.6 | mg |
| | Pantothenic acid | 1.0 | mg |
| | Folic acid | 50 | μg |
| | Vitamin C | 45 | mg |
| | α-Carotene | 0.8 | μg |
| | β-Carotene | 4.2 | μg |
| | Lycopene | 1.4 | μg |
| | Lutein | 5.6 | μg |
| Mineral | Sodium chloride | 100 | mg |
| | Potassium hydroxide | 100 | mg |
| | Potassium dihydrogen phosphate | 20 | mg |
| | Chromium yeast | 2 | mg |
| | Zinc yeast | 5 | mg |
| | Trisodium citrate dihydrate | 100 | mg |
| | Ferrous sulfate | 5 | mg |

Example 4

Preparation of Powdery Nutritional Composition

In an evaporator, 53 kg of a liquid nutritional composition prepared in accordance with the amounts of raw materials shown above in Table 3 was concentrated into 32 kg. The resulting nutritional composition concentrate was treated by a spray drier (exhaust air temperature: 95° C., Orifice No. 74, Core No. 17), whereby 10 kg of powdery nutritional composition was obtained. Meibalance C (Table 4) and Glucerna (Table 5) were treated in a manner similar to the above, whereby powders for control were obtained. The solid contents of the powdery nutritional composition, Glucerna and Meibalance C were 96.7%, 95.3% and 96.3%, respectively. The energy content per g of the powdery nutritional composition, Glucerna and Meibalance C powder were 5.6 kcal, 5.5 kcal and 4.6 kcal, respectively.

TABLE 4

Meibalance C

| Component | Raw materials | In 100 g basic mixture | |
|---|---|---|---|
| Protein | Milk protein concentrate (MPC) | 4 | g |
| Carbohydrate | Dextrin | 14.2 | g |
| | Sucrose | 0.4 | g |
| Lipid | Plant oil | 2.8 | g |
| Food fiber | Sparingly digestible dextrin | 1 | g |
| Mineral | Potassium | 100 | mg |
| | Sodium | 110 | mg |
| | Chlorine | 140 | mg |
| | Calcium | 110 | mg |
| | Phosphorous | 85 | mg |
| | Magnesium | 15 | mg |
| | Iron | 1 | mg |
| Vitamin | Vitamin A | 200 | IU |
| | Vitamin D | 20 | IU |
| | Vitamin E | 3 | mg |
| | Vitamin $B_1$ | 0.15 | mg |
| | Vitamin $B_2$ | 0.2 | mg |

TABLE 4-continued

Meibalance C

| Component | Raw materials | In 100 g basic mixture | |
|---|---|---|---|
| | Vitamin $B_6$ | 0.3 | mg |
| | Vitamin $B_{12}$ | 0.6 | μg |
| | Niacin | 1.6 | mg |
| | Pantothenic acid | 0.6 | mg |
| | Folic acid | 50 | μg |
| | Vitamin C | 16 | mg |

TABLE 5

Glucerna

| Component | Raw materials | In 100 g basic mixture | |
|---|---|---|---|
| Protein | Casein | 4.2 | g |
| Carbohydrate | Maltodextrin | 6.2 | g |
| | Fructose | 1.7 | g |
| Lipid | Sunflower oil + soybean oil + soybean lecithin | 5.56 | g |
| Food fiber | Soybean polysaccharide | 1.4 | g |
| Mineral | Potassium | 156 | mg |
| | Sodium | 93.2 | mg |
| | Chlorine | 144 | mg |
| | Calcium | 70 | mg |
| | Phosphorous | 70 | mg |
| | Magnesium | 28 | mg |
| | Iron | 1.4 | mg |
| Vitamin | Vitamin A | 352 | IU |
| | Vitamin D | 28 | IU |
| | Vitamin E | 3.2 | IU |
| | Vitamin $B_1$ | 0.16 | mg |
| | Vitamin $B_2$ | 0.18 | mg |
| | Vitamin $B_6$ | 0.22 | mg |
| | Vitamin $B_{12}$ | 0.64 | μg |
| | Niacin | 2.12 | mg |
| | Pantothenic acid | 0.92 | mg |
| | Folic acid | 42 | μg |
| | Vitamin C | 21.2 | mg |

Example 5

Process for Solidifying Nutritional Composition

To 120 g of the powdery nutritional composition prepared in Example 4 was added 2 g of agar ("Agar Quick", trade name; product of Ina Shokuhin), followed by the addition of 150 mL of hot water (about 60° C.). The mixture was stirred. After heat treatment of the reaction mixture for 5 minutes in a microwave oven ("RE-BM5W", trade name; product of SAMSUNG) at 500 W rated high-frequency output, it was solidified by placement in a refrigerator. The resulting nutritional composition has a calorie content of 672 kcal. This calorie content can be adjusted as needed. The agar concentration is preferably 0.5 to 2%.

Test 1 (Influence on the Blood Sugar Level of Normal Rat)

(1) After preliminary breeding of 5-week-old Spraque-Dawley IGS male rats (Charles River, Japan) for 2 weeks, they were provided for the test as 7-week-old rats. The rats were fasted for 18 hours and then, classified into two groups (n=6), a group to which the composition prepared in Example 1 was to be administered and a control group to which Glucerna was to be administered so that the average of the blood sugar level would be equal between these two groups.

To these two groups, 12.5 mL/kg of the composition prepared in Example 1 and Glucerna were orally administered compulsorily through a probe, respectively. The blood sugar levels of the caudal vein just before administration (0 minute) and 30 minutes, 60 minutes, 90 minutes and 120 minutes after the administration were measured using a small electrode type blood sugar level monitor ("Antosense II", trade name; product of Bayer-Sankyo). Glucerna (product of Dynabbott) was found to have protein, lipid and carbohydrate at an energy percentage of 16.4%, 49.2% and 34.4% (255 kcal/250 mL), respectively. The results are shown in FIG. 1.

According to measurements of the change in blood sugar levels between the Glucerna administered group and the nutritional composition administered group, the blood sugar level of the former group increased to about 130 mg/dL 30 minutes after administration, while the blood sugar level of the latter group increased only to about 110 mg/dL. This suggests that a rise in the blood sugar level was significantly suppressed by the administration of the nutritional composition, compared with Glucerna.

(2) After preliminary breeding of 6-week-old Spraque-Dawley (SD) male rats (Japan SLC) for 1 week, they were provided for the test as 7-week-old rats. The rats were fasted for 18 hours and then, classified into two groups (n=6), that is, a group to which the composition prepared in Example 2 was to be administered and a control group to which Meibalance C ("trade name" product of Meiji Milk Products) was to be administered so that the average of the blood sugar level would be equal between these two groups. Meibalance C has a calorie content of 100 kcal/100 mL and contains protein, lipid and carbohydrate at an energy percentage of 16%, 25% and 59%.

Figure 2:
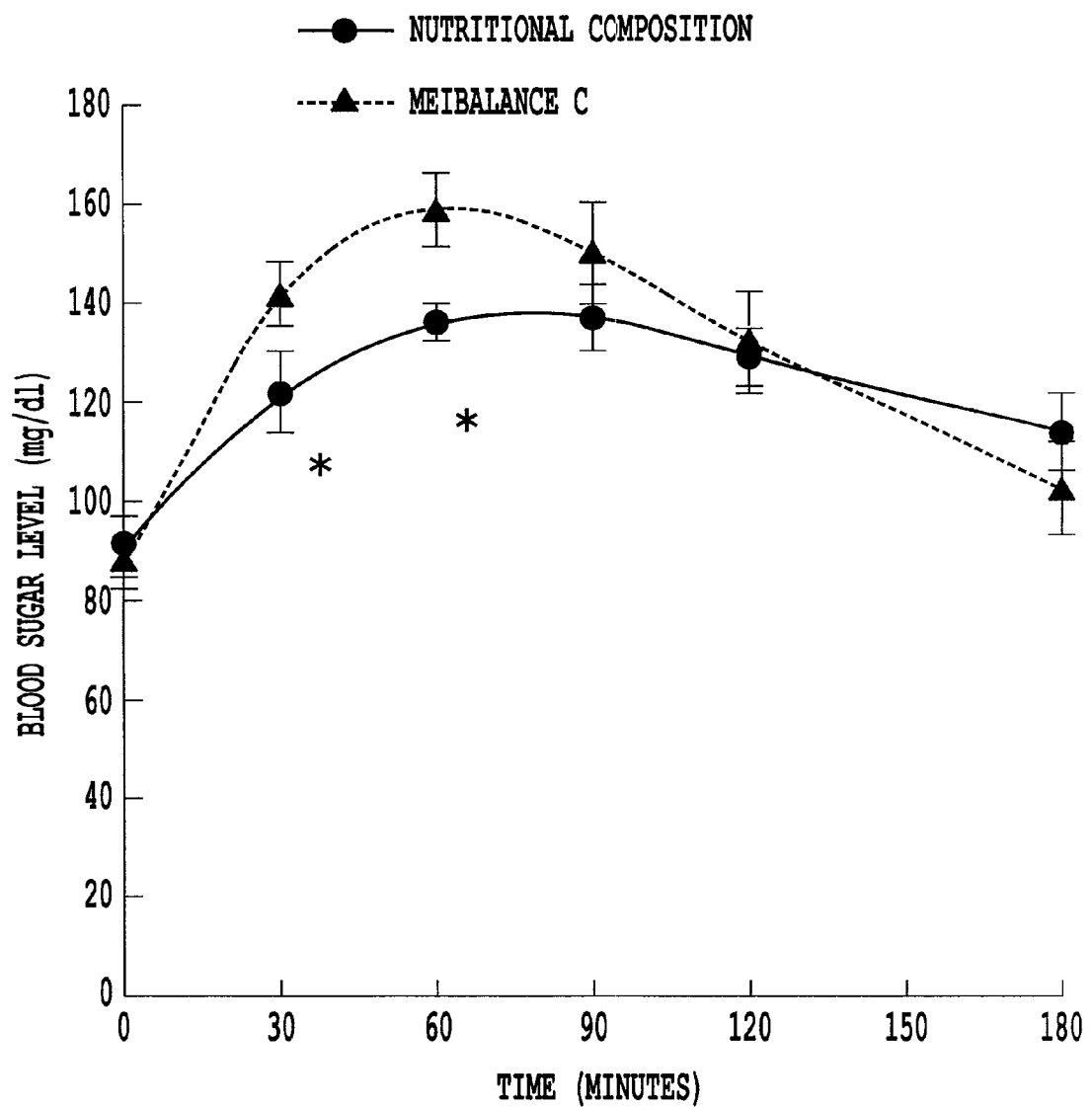
FIG. 2 is a graph showing a change in the blood sugar level after single oral administration of each of the nutritional composition and Meibalance C to normal rats. In the diagram, (-●-) means the nutritional composition, while (••▲••) means Meibalance C. Each point is a mean±standard deviation (n=6). *: P<0.05: Significant difference from Meibalance C (Student-t Test).

To these two groups, the nutritional composition and Meibalance C, each 12.5 mL/kg (12.5 kcal/kg), were separately and compulsorily administered p.o. through a probe. The blood sugar levels of the caudal vein just before administration (0 minute) and 30 minutes, 60 minutes, 90 minutes, 120 minutes and 180 minutes after administration were measured. The results are shown in FIG. 2. The value of each group thus measured was indicated by mean±standard deviation (Mean±SE). A significant difference between groups was detected by Student-t test and that less than 5% was judged significant.

According to the comparison in a time-dependent change in the blood sugar level between the Meibalance C administered group and the nutritional composition administered group, the blood sugar level of the former one increased to about 140 to 160 mg/dL 30 to 60 minutes after administration, while that of the latter group increased only to about 120 mg/dL after 30 minutes and about 140 mg/dL after 60 minutes. This suggests that the rise in the blood sugar level was significantly suppressed, compared with Meibalance C.

It has been found based on the above-described results that the nutritional composition of the present invention is effective for significantly suppressing a postprandial rise in the blood sugar level of normal rats compared with the existing ordinarily used fluid diet.

(3) The blood-level-rise suppressing effect of each of the nutritional composition prepared in Example 3, and Glucerna and Meibalance C, as a control, was studied using normal rats. After preliminary breeding of 6-week-old Spraque-Dawley (SD) male rats (Japan SLC) for 1 week with "CRF-1" (trade name; product of Oriental Yeast Industry), they were provided for the test as 7-week-old rats. The rats were fasted for 18 hours, followed by measurement of the blood sugar level of each caudal vein. They were then classified into three groups (n=6), that is, a group to which the composition was to be administered and, as two control groups, a group to which Glucerna was to be administered and a group to which Meibalance C was to be administered so that the average of the blood sugar level would be equal among these three groups.

Figure 3:
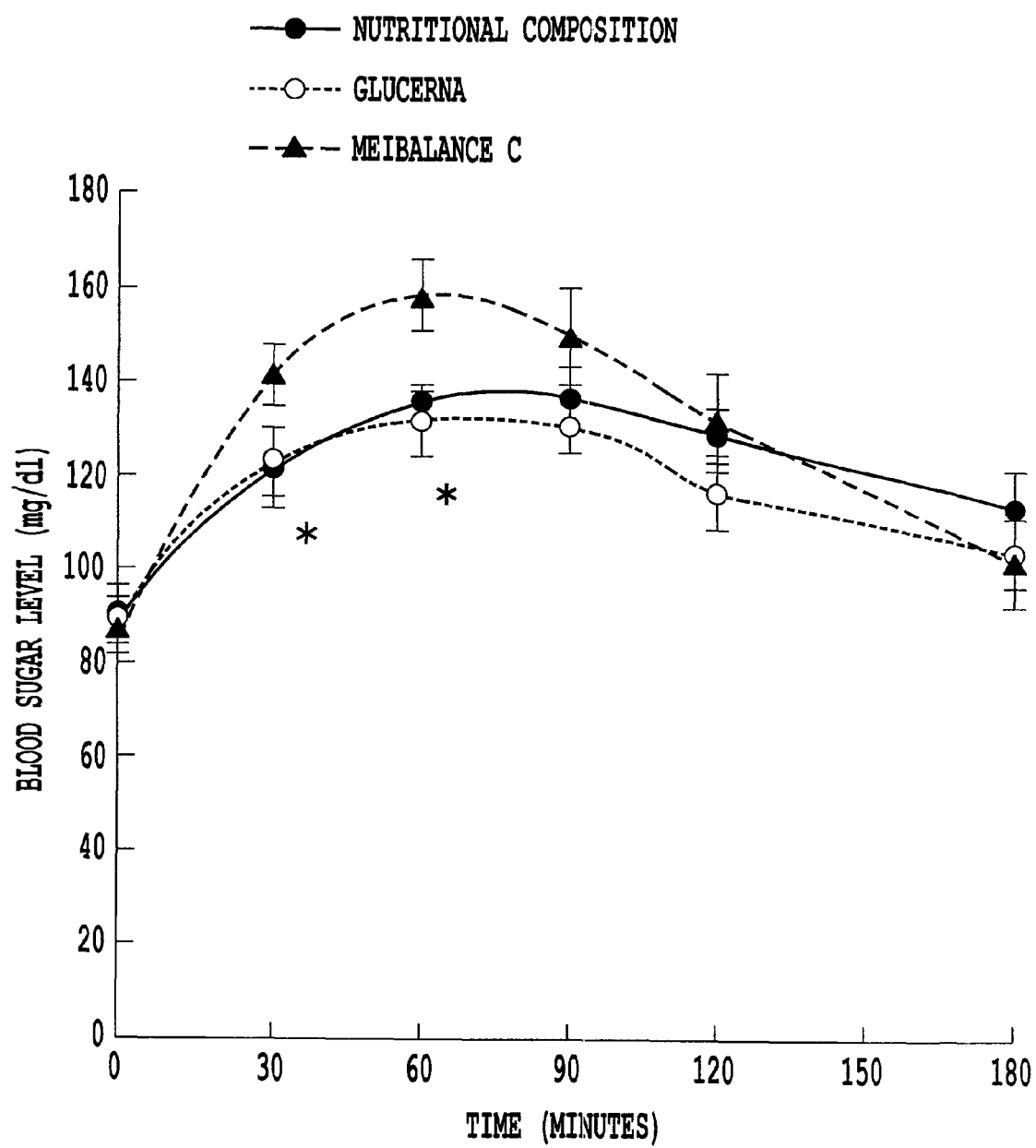
FIG. 3 is a graph showing a change in the blood sugar level after single oral administration of each of the nutritional compositions, Glucerna and Meibalance C to normal rats. In the diagram, (-●-) means the nutritional composition, (••○••) means Glucerna and (••▲••) means Meibalance C. Each point is a mean±standard deviation (n=6). *: P<0.05: Significant difference from Meibalance C (Student-t Test).

To these three groups, the nutritional composition, Glucerna or Meibalance C, each in an amount of 12.5 mL/kg (12.5 kcal/kg), were compulsorily administered p.o. through a probe. The blood sugar levels of the caudal vein just before administration (0 minute) and 30 minutes, 60 minutes, 90 minutes, 120 minutes and 180 minutes after the administration were measured (they were food- and water-fasted after administration of the test substance). The value of each group thus measured is indicated by mean±standard deviation (Mean±SE). A significant difference between groups was detected by Student-t test and that less than 5% was judged significant. The results are shown in FIG. 3.

The blood sugar level of each of the nutritional composition administered group and the Glucerna administered group showed a change within a range of almost 90 to 130 mg/dL for 0 to 60 minutes. The blood sugar level of the Meibalance C administered group increased to about 140 to 160 mg/DL after 30 to 60 minutes, thus showing a significant rise relative to the nutritional composition administered group.

The nutritional composition of the present invention exhibited a similar effect to Glucerna in suppression of a postprandial rise in the blood level of normal rats by administration at their fasting time.

Test 2 (Effects on the Blood Sugar Level of Streptozotocin Induced Type I Diabetes)

(1) After preliminary breeding of 6-week-old Spraque-Dawley (SD) male rats (Japan SLC) with an ordinary diet ("CRF-1", trade name; product of Oriental Yeast Industry), they were provided for the test as 7 week old rats. Just after Streptozotocin (STZ) (product of Wako Pure Chemicals) was dissolved in a citrate buffer (pH 4.5, 0.05M) at a concentration of 14 mg/mL, 70 mg/5 mL/kg of the resulting solution was intraperitoneally injected. For one week after administration of STZ, the rats were fed with ordinary feed and water. From the next evening, they were fasted for 18 hours (water ad libitum) and then, the blood sugar level of the caudal vein was measured. They were classified into two groups (n=6), that is, a group to which the composition prepared in Example 2 was to be administered and a control group to which Meibalance C was to be administered so that the average of the blood sugar level of these two groups would be equal.

Figure 4:
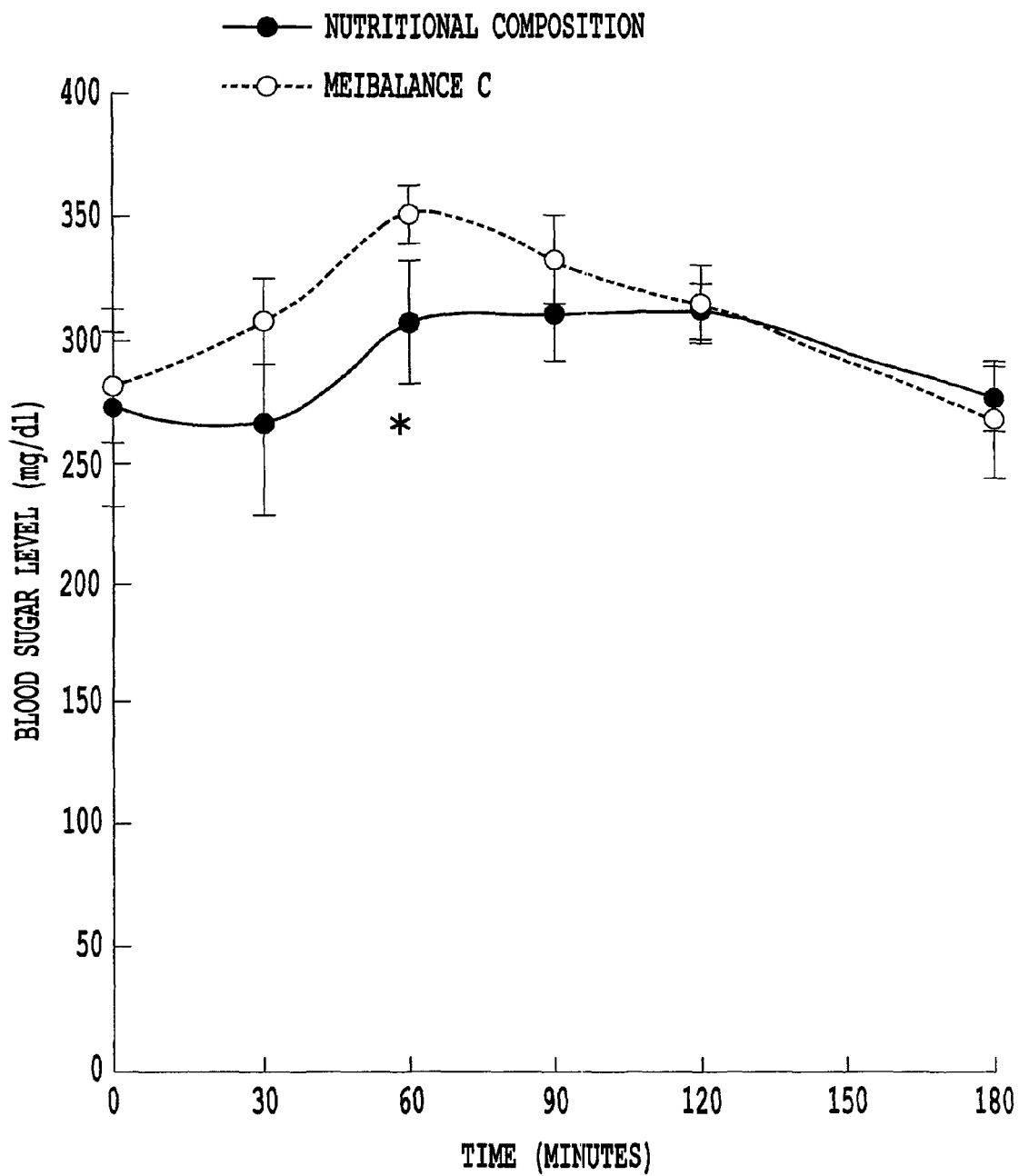
FIG. 4 is a graph showing a change in the blood sugar level after oral administration of each nutritional composition and Meibalance C to Streptozocin-induced diabetic rats. In the diagram, (••●••) means the nutritional composition, while (••○••) means Meibalance C. Each point is a mean±standard deviation (n=6). *: P<0.05: Significant difference from Meibalance C (Student-t Test).

To these two groups, the nutritional composition and Meibalance C, each in amounts of 12.5 mL/kg (12.5 kcal/kg), were compulsorily administered p.o. through a probe. The blood sugar levels of the caudal vein just before administration (0 minute) and 30 minutes, 60 minutes, 90 minutes, 120 minutes and 180 minutes after the administration were measured. Meibalance C has a calorie content of 100 kcal/100 mL and contains protein, lipid and carbohydrate at an energy percentage of 16%, 25% and 59%. The results are shown in FIG. 4. The value of each group thus measured was indicated by mean±standard deviation (Mean±SE). A significant difference between groups was detected by Student-t test and that less than 5% was judged significant.

According to the comparison of the time-dependent change in the blood sugar level between Meibalance C and the nutritional composition administered groups, the blood sugar level of the former group showed a gradual increase to about 350 mg/dL after 60 minutes, while that of the latter group was almost the same level, with a little change observed during 60 to 120 minutes after administration and after 60 minutes, suggesting that a rise in the blood sugar level was significantly suppressed, compared with the former group.

STZ-induced diabetes is an insulin-deficient experimental diabetic model which exhibits high blood sugar level by selectively destroying B cells in the pancreas (Steiner, H. et al.: Diabetologia, 6, 558, 1970; Hoftiezer, V. and Carpenter, A. M.: Diabetologia, 9, 178, 1973). The pancreatic B-cell disturbing effect of STZ can be adjusted by its dose. When the pancreatic B cells are destroyed and cannot be regenerated, low insulinemia and marked hyperglycemia onset (Blondel, O. et al.: Diabetes, 38, 610, 1989). This morbid state is similar to that of insulin-dependent type I diabetes (IDDM).

It has been confirmed based on the test results using STZ induced diabetic rats that the nutritional composition of the present invention was also effective for decreasing the blood sugar level rise in insulin deficient I type diabetes compared with the existing ordinary fluid diet.

(2) After preliminary breeding of 6-week-old Spraque-Dawley (SD) male rats (Japan SLC) with an ordinary diet ("CRF-1", trade name; product of Oriental Yeast Industry) for one week, they were provided for the test as 7 week old rats. Just after Streptozotocin (STZ) (product of Wako Pure Chemicals) was dissolved in a citrate buffer (pH 4.5, 0.05M) to give a concentration of 14 mg/mL, 70 mg/5 mL/kg of the resulting solution was intraperitoneally injected to the rats. For seven days after administration of STZ, the rats were fed with ordinary feed and water. From the next evening, the rats were fasted for 18 hours (with water ad libitum) and then, the blood sugar level of the caudal vein was measured. They were classified into three groups (n=6), that is, a group to which the nutritional composition prepared in Example 2 was administered and two control groups, a Glucerna administered group and a Meibalance C administered group, so that the average blood sugar level would be equal (260 to 270 mg/dL) among these three groups.

Figure 5:
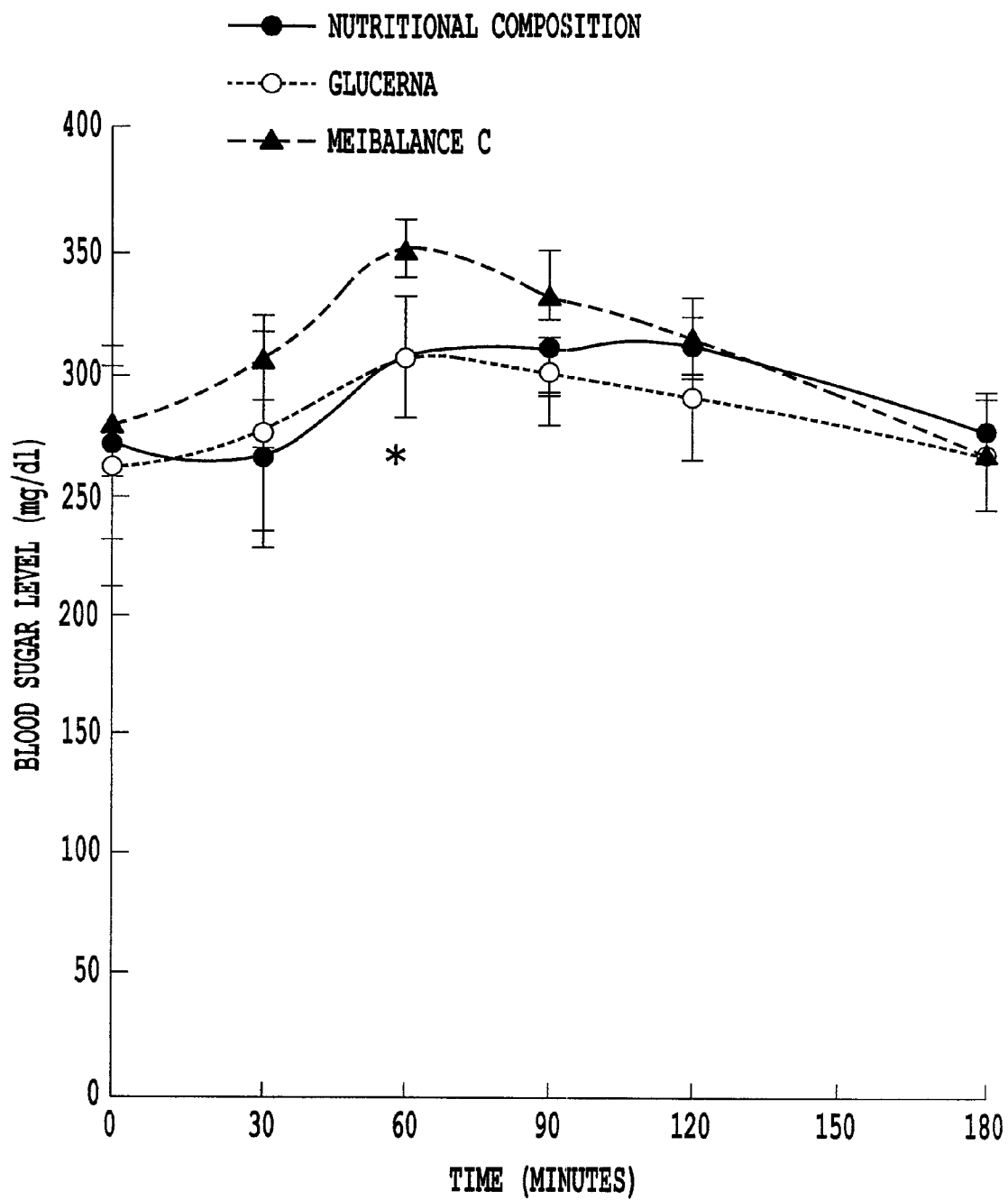
FIG. 5 is a graph showing a change in the blood sugar level after single oral administration of each nutritional composition, Glucerna and Meibalance C to Streptozocin-induced diabetic rats. In the diagram, (-●-) means the nutritional composition, (••○••) means Glucerna and (••▲••) means Meibalance C. Each point is a mean±standard deviation (n=6). *: P<0.05: Significant difference from Meibalance C (Student-t Test).

To these three groups, the nutritional composition, Glucerna or Meibalance C, each in an amount of 12.5 mL/kg (12.5 kcal/kg), were compulsorily administered p.o. through a probe. The blood sugar levels of the caudal vein just before administration (0 minute) and 30 minutes, 60 minutes, 90 minutes, 120 minutes and 180 minutes after the administration were measured. The value of each group thus measured was indicated by mean±standard deviation (Mean±SE). A significant difference between groups was detected by Student-t test and that less than 5% was judged significant. The results are shown in FIG. 5.

The blood sugar level of the nutritional composition administered group showed a small increase from 270 mg/dL to 300 mg/dL sixty minutes after administration, stayed at almost the same value until 120 minutes and after 180 minutes, it fell to the same value as before administration. The blood sugar level of the Glucerna administered group showed a similar pattern to that of the nutritional composition administered group. The blood sugar level of the Meibalance C administered group, on the other hand, showed an increase from 270 mg/dL to 350 mg/dL sixty minutes after administration and after 180 minutes, it lowered even to the same value to that of the nutritional composition or Glucerna administered group.

In short, the nutritional composition of the present invention suppresses the rise in the blood sugar level of a diabetic model animal to similar extents as that of Glucerna, and significantly suppresses a rise in the blood sugar level compared with Meibalance C which is a commercial general fluid diet. As a result, it has been confirmed that the nutritional composition of the present invention is effective for suppressing a rise in the blood sugar level in insulin-deficient type I diabetes (IDDM).

Test 3 (Effects on Spontaneous Type II Diabetes (GK Rats))

(1) After preliminary breeding of 5-week-old male GK rats (CLEA Japan) for 2 weeks with an ordinary diet ("CRF-1", trade name; product of Oriental Yeast Industry), they were provided for the test as 7-week-old rats. They were then classified into three groups (n=6), that is, a group to which the nutritional composition prepared in Example 3 was to be administered and two control groups which were a Glucerna administered group and a Meibalance C administered group so that the average of the blood sugar level would be equal among these three groups.

Figure 6:
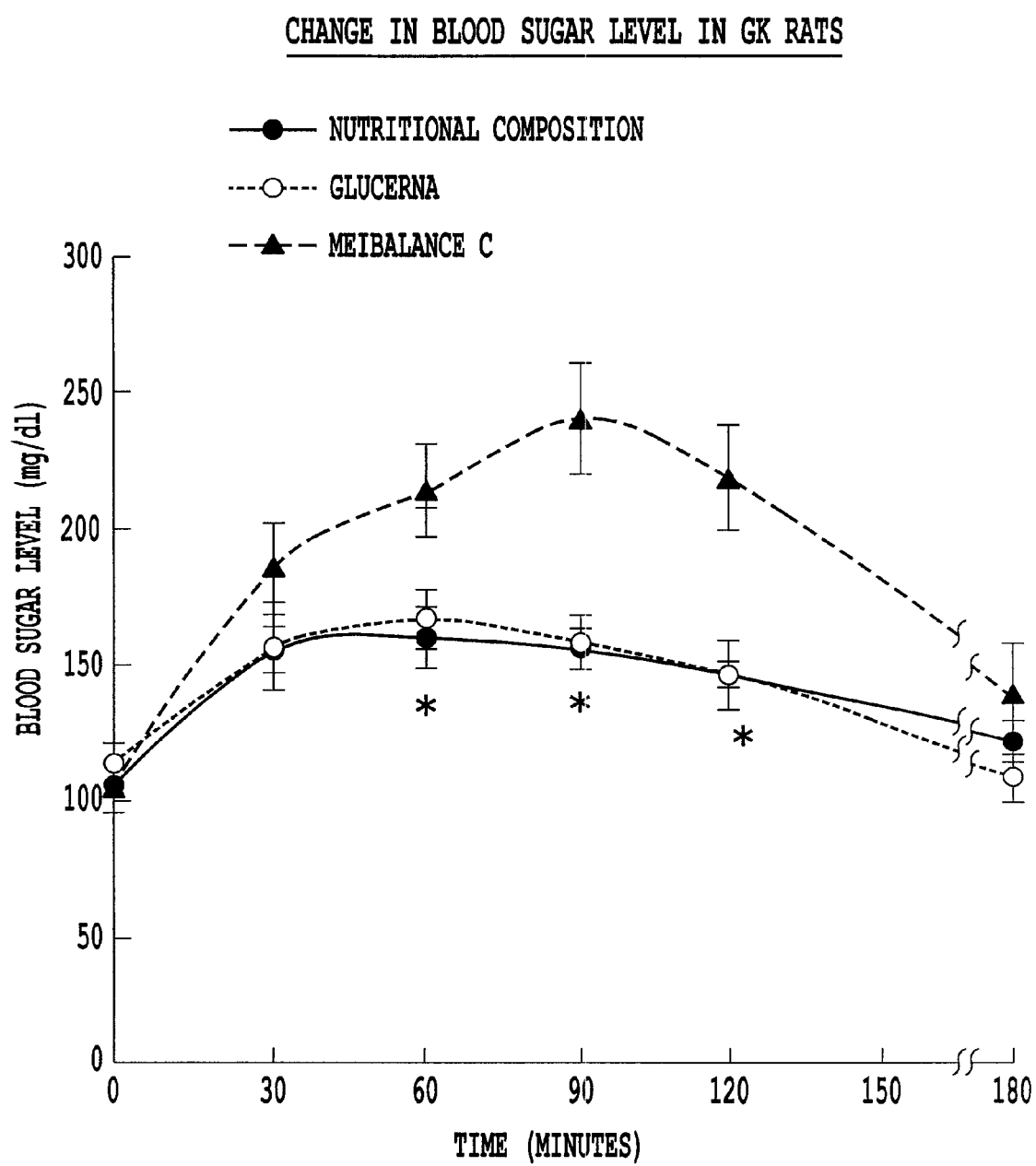
FIG. 6 is a graph showing a change in the blood sugar level after single oral administration of one of the following: the nutritional composition, Glucerna or Meibalance C, to GK rats. In the diagram, (-●-) means the nutritional composition, (••○••) means Glucerna and (••▲••) means Meibalance C. Each point is a mean±standard deviation (n=6). *: P<0.05: Significant difference from Meibalance C (Student-t Test).

After the rats were fasted for 18 hours, the nutritional composition, Glucerna and Meibalance C, each in an amount of 12.5 mL/kg, were compulsorily administered p.o. through a probe, respectively. The blood sugar levels of the caudal vein just before administration and 30 minutes, 60 minutes, 90 minutes, 120 minutes and 180 minutes after administration were measured. The value of each group thus measured was indicated by mean±standard deviation (Mean±SE). A significant difference between groups was detected by Student-t test and that less than 5% was judged significant. The results are shown in FIG. 6.

The blood sugar level of both the nutritional composition administered group and Glucerna administered group showed an increase with a slow pace from about 100 mg/dL to 150 mg/dL within thirty minutes after administration, and remained at around 150 mg/dL until 120 minutes after that. Thus, no significant difference between these groups was seen. The blood sugar level of the Meibalance C administered group showed an increase to about 210 mg/dL after 60 minutes. Compared with the nutritional composition and Glucerna administered groups, a blood sugar level of the Meibalance C administered group showed a significant increase, and this continued until 120 minutes.

GK rats are spontaneous diabetic model animals made by selective breeding of Wister rats aimed at lowering in glucose tolerance (Goto Y. et al.: Proc. Jap. Acad., 51:80, 1975; Goto Y. et al.: Tohoku J. Exp. Med., 119: 85, 1976). From these rats, no obesity was recognized, while hyperglycemia, lowering in glucose tolerance and glucose-stimulated lowering in initial insulin secretion were recognized (Goto Y. Kakizaki M.: Proc. Jap. Acad., 57:381, 1981; Kimura K. et al.: Tohoku J. Exp. Med., 137:453, 1982:; Toyota T. et al.: Diabetologia, 14: 319, 1987; Sugiyama Yasuo, et al.: Diabetes 32:593, 1989). Their morbidity is much similar to that in the human non-pyknic non-insulin-dependent type II diabetes, so they are used as animal model for NIDDM.

The nutritional composition of the present invention significantly suppressed the rise in blood sugar level, which is otherwise observed when an ordinary fluid diet is orally administered to GK rats, and its suppression degree is almost similar to that of Glucerna. This suggests that the nutritional composition of the present invention is useful for nutritional management and blood sugar level control of type II diabetes, which accounts for about 95% of all diabetes cases.

From the above-described test results, it has been confirmed that the nutritional composition of the present invention features, different from the conventional nutritional compositions, a slow rise in the blood sugar level after intake, suppression of a blood sugar level rise by acting on insulin deficient type I diabetes and insulin resistance type II diabetes and improvement in lipid metabolism.

Test 4 (Long-term Administration Effect on Spontaneous Type II Diabetes)

As test animals, 7-week-old C57BL/KSJ-db/db Jcl mice (male) were purchased (from CLEA Japan). Their use as 8-week-old mice was started after habituation for one week with an ordinary diet ("CRF-1", trade name; product of Oriental Yeast Industry). The blood sugar level and HbA1c ("DCA2000 System", trade name; product of Bayer Medical) of the mice at feeding state with the ordinary diet were measured. They were then classified into three groups (n=8), that is, a powdery nutritional composition administered group, a Glucerna powder administered group and a Meibalance C powder administered group so that the average blood sugar level would be equal among these three groups (values upon classification are regarded as those of Day 0). For 9 weeks from the next day after classification, these three groups were fed ad libitum with water, and the nutritional composition prepared in Example 4, Glucerna and Meibalance C powder, respectively, instead of the ordinary diet. The intake energy of each group was calculated from each of the intake amounts of the nutritional composition, Glucerna and Meibalance C.

After feeding ad libitum, the blood sugar level and hemoglobin A1c (HbA1c), which are indexes of the diabetic morbidity, were measured periodically (once/week, at 2:00 to 4:00 pm). The HbA1c is glucose-bound hemoglobin. In human beings, the blood sugar level represents the instant value when the blood is collected. On the other hand, the HbA1c reflects the controlled condition of the blood sugar level for 1 to 3 months prior to the blood collection time so that it is utilized in medical facilities for examination for judging the appropriateness of the long-term blood sugar control.

After the mice were fed ad libitum for 9 weeks, they were fasted for 18 hours (with only water fed ad libitum). They were then anesthetized with diethyl ether, followed by blood collection and anatomy. From the blood, the serum was separated and serum GOT and serum GPT were measured by "DRI-CHM 3500" (trade name; product of FUJI FILM). The liver was excised and from it, lipid was extracted in accordance with the method of Folch, et al. The neutral fat accumulation in the liver was quantitatively analyzed as a lipid component by "Iatroscan" (trade name; product of Iatron Laboratories, Inc). As a primary developing solvent, a 50:20:2.5 mixture of chloroform, methanol and water was used, while as a secondary developing solvent, a 60:5:0.15 mixture of hexane, diethyl ether and formic acid were used.

The measuring results were indicated as a mean±standard deviation (Mean±S.D.). A difference among three groups less than 5% was judged significant in accordance by the Mann-Whitney U test.

<Results>

Figure 7:
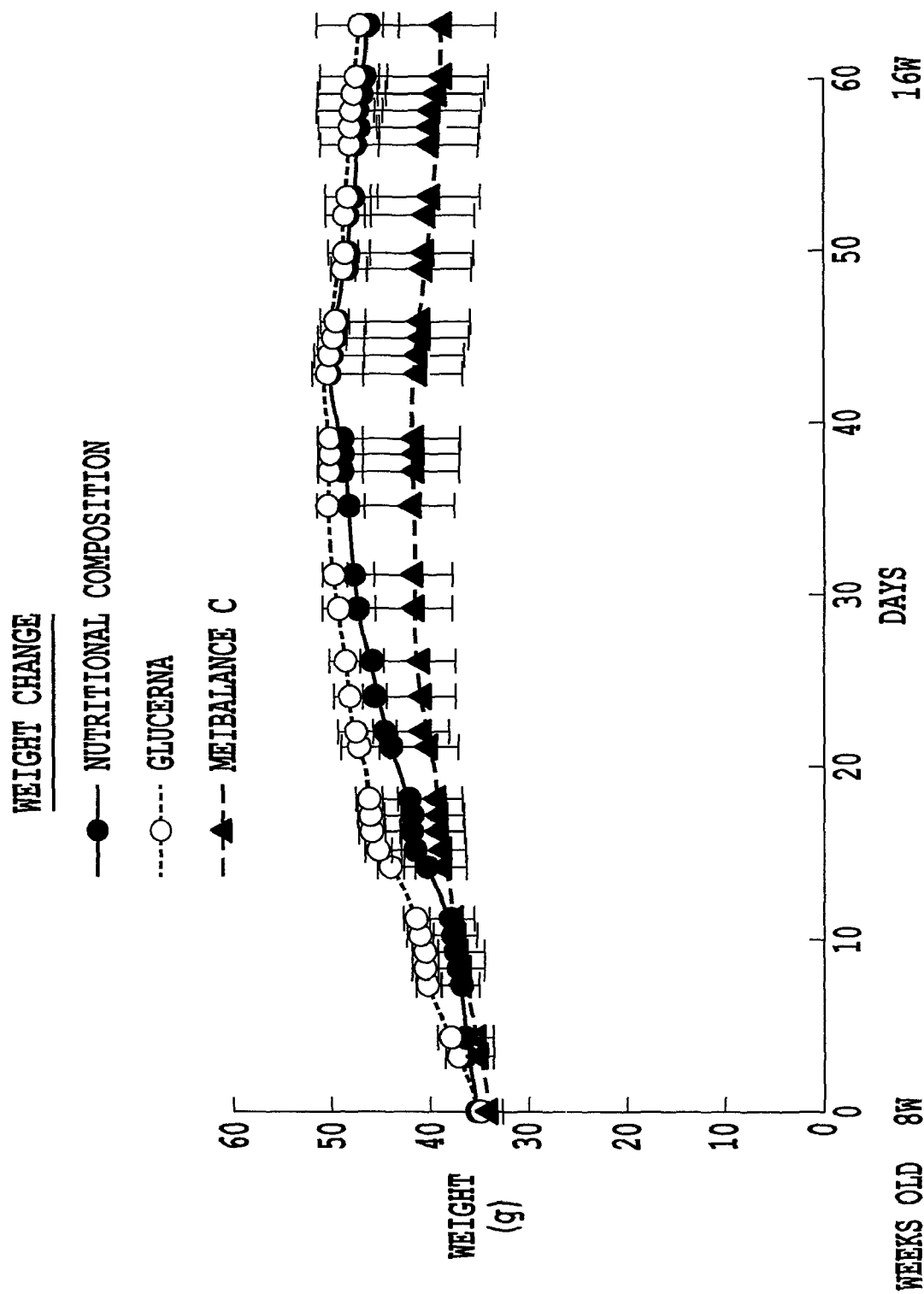
FIG. 7 is a graph showing a weight change of C57BL/Ksj-db/db jcl mice, which are spontaneous diabetic model mice, after they were fed ad libitum with one of the following: the nutritional composition, Glucerna or Meibalance C powder, for 9 weeks. In the diagram, (-●-) means the nutritional composition, (••○••) means Glucerna and (••▲••) means Meibalance C. Each point is a mean value±standard deviation (n=8).

The intake energy of the nutritional composition group showed almost a stable change for 9 weeks. On the other hand, that of the Glucerna group gradually decreased from three weeks after the intake was started, while that of the Meibalance C group started to lower from 4 weeks after the intake and became the same level with that of the Glucerna group from 5 weeks to 8 weeks. The weight change for 9 weeks is shown in FIG. 7.

The nutritional composition and Glucerna powder intake groups showed higher weight increasing tendencies throughout the term than the Meibalance C powder intake group.

Figure 8:
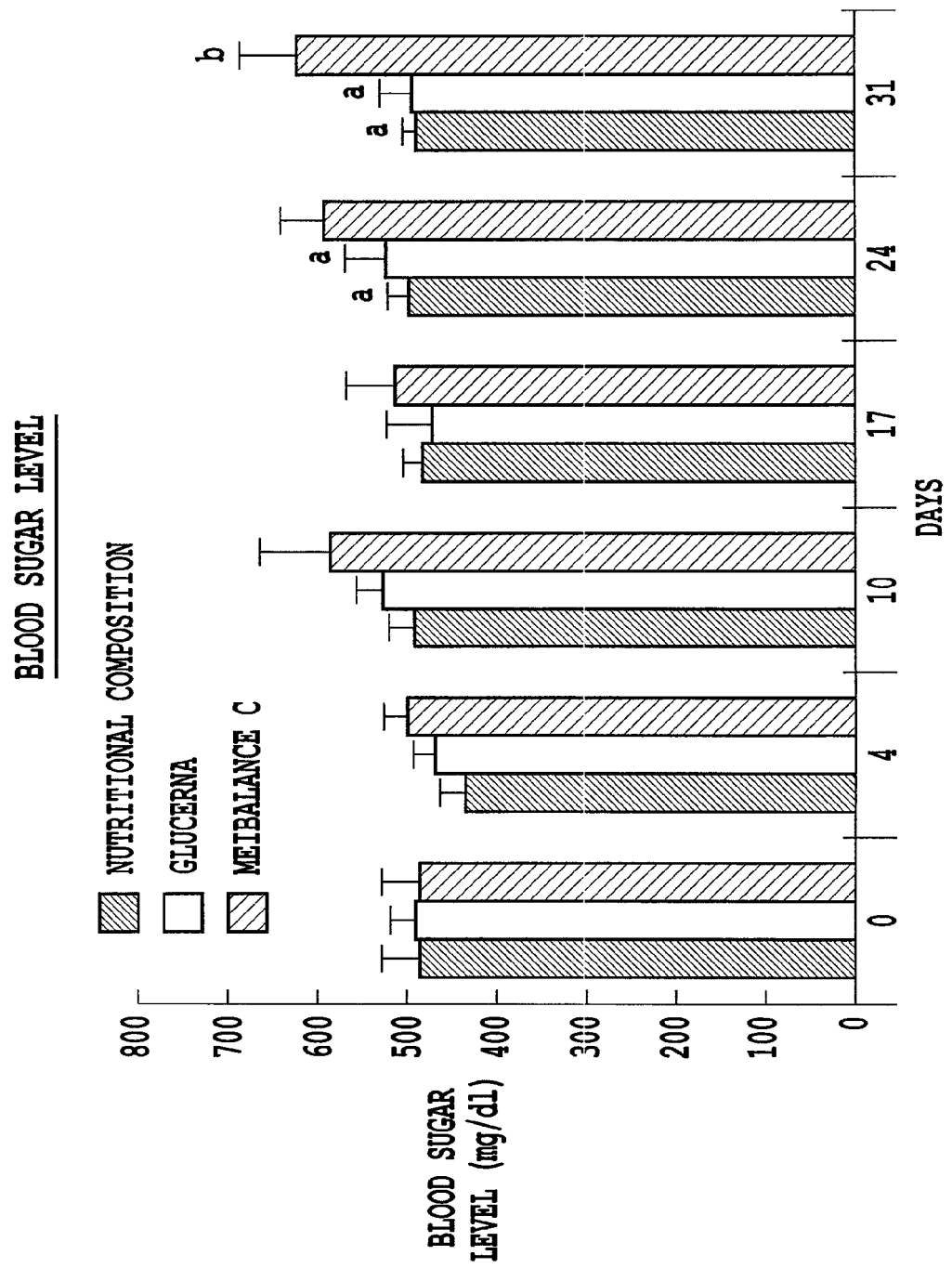
FIG. 8 is a graph showing a change in the blood sugar level of mice similar in kind to the above-described ones after they were fed ad libitum with one of the following: the nutritional composition, Glucerna or Meibalance C powder for 31 days. In the diagram, (■) means the nutritional composition, (□) means Glucerna and (♦) means Meibalance C. Each point is a mean±standard deviation (n=8). *P<0.05: no significant difference when the letter is the same (Mann-Whitney U-test).

The blood sugar levels of the nutritional composition and Glucerna powder intake groups showed similar changes. For around four weeks, the blood sugar level did not change from around 500 mg/dL, which was the same value as before intake was started. The blood sugar level of the Meibalance C intake group, on the other hand, increased one week or so after the start of intake and became significantly high after 3 to 4 weeks compared with that of the nutritional composition. The results are shown in FIG. 8.

Figure 9:
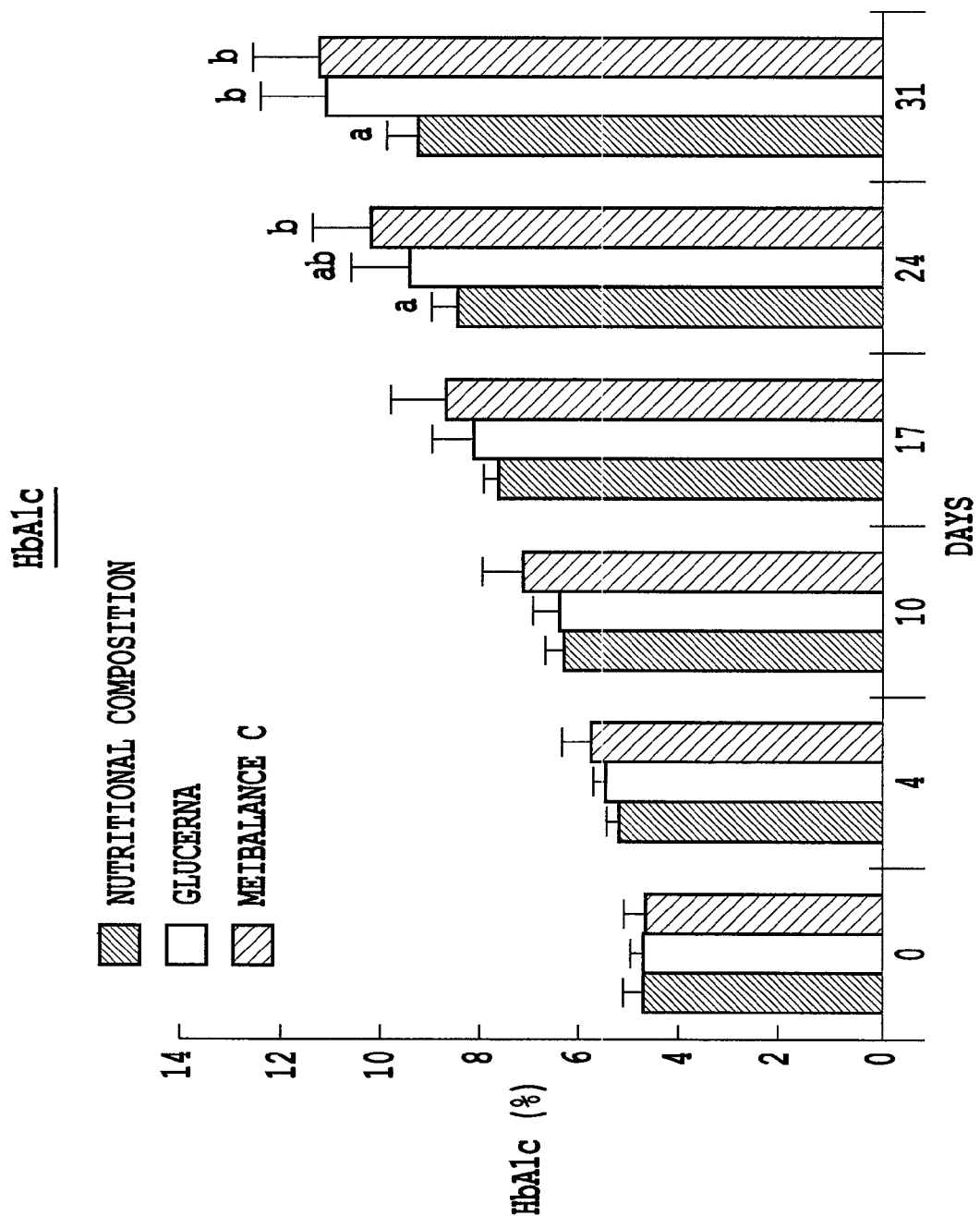
FIG. 9 is a graph showing a change in the HbA1c level of mice similar in kind to the above-described mice, after they were fed ad libitum with one of the following: the nutritional composition, Glucerna and Meibalance C powder for 31 days. In the diagram, (■) means the nutritional composition, (□) means Glucerna and (♦) means Meibalance C. Each point is a mean±standard deviation (n=8). *P<0.05: no significant difference when the letter is the same (Mann-Whitney U-test).

In all the groups, HbA1c showed a tendency to increase until on and around Day 17. On Day 24, HbA1c of the nutritional composition group became significantly low compared with the Meibalance C group and on Day 31, that of the nutritional composition group became significantly low compared with those of the Glucerna and Meibalance C groups. The results are shown in FIG. 9.

On Week 5, the blood sugar level in the Meibalance C group exceeded the measurable limit. On Week 6, measurement was stopped because the blood sugar level and HbA1c in both the Glucerna and Meibalance C groups exceeded the measurable limits.

Figure 11:
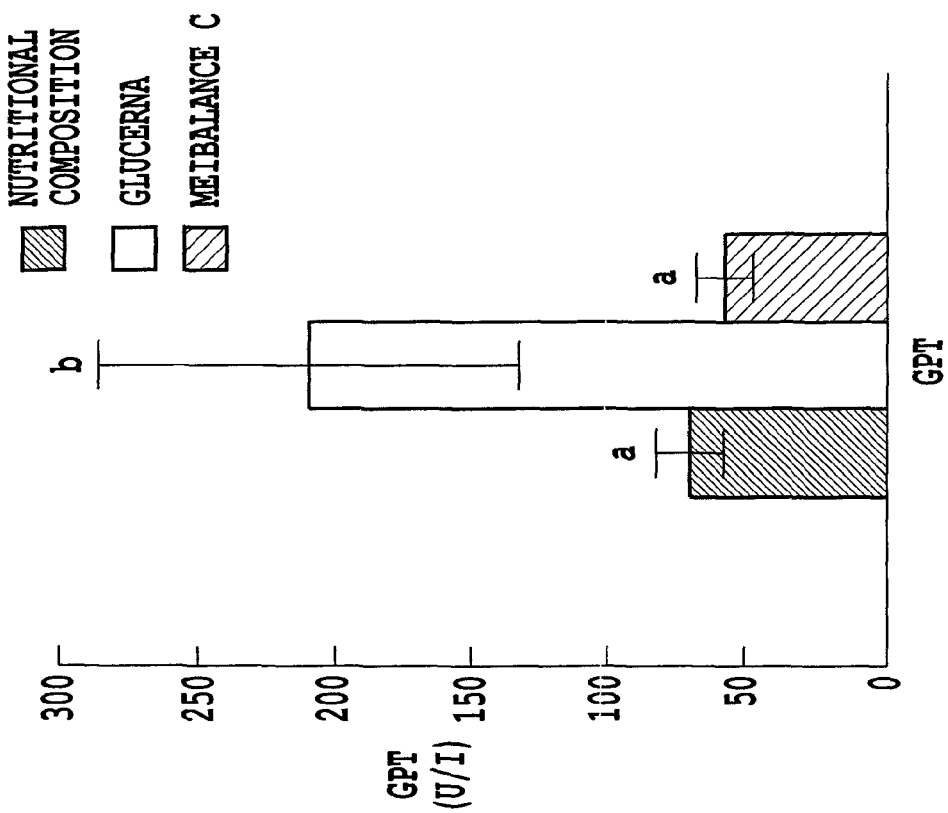
FIG. 11 is a graph showing serum GPT levels of mice similar in kind to the above-described mice, after they were fed ad libitum with one of the following: the nutritional composition, Glucerna or Meibalance C powder for 9 weeks. In the diagram, (■) means the nutritional composition, (□) means Glucerna and (♦) means Meibalance C. Each point is a mean±standard deviation (n=8). *P<0.05: no significant difference when the letter is the same (Mann-Whitney U-test).
Figure 10:
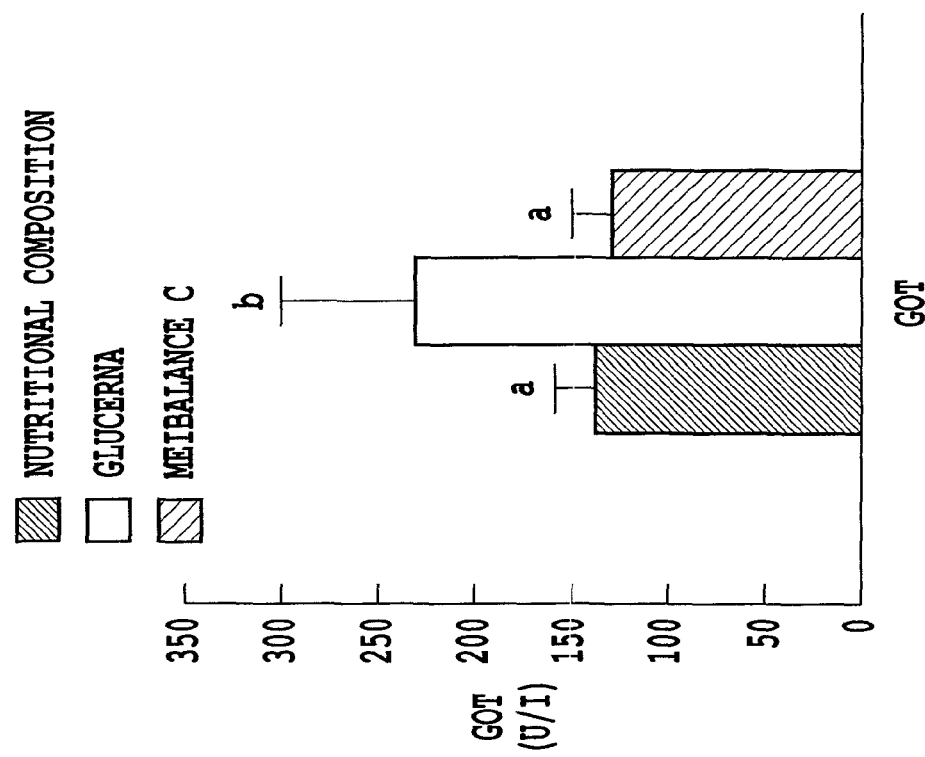
FIG. 10 is a graph showing serum GOT level of mice similar in kind to the above-described mice, after they were fed ad libitum with one of the following: the nutritional composition, Glucerna or Meibalance C powder for 9 weeks. In the diagram, (■) means the nutritional composition, (□) means Glucerna and (♦) means Meibalance C. Each point is a mean±standard deviation (n=8). *P<0.05: no significant difference when the letter is the same (Mann-Whitney U-test).

After feeding with each powder for 9 weeks and then fasting overnight (18 hours), the mice were subjected to blood collection and anatomy. The serum GOT and GPT, and neutral fat accumulation amount in the liver were measured. The GOT and GPT of the Glucerna group showed a significantly high value relative to those of the nutritional composition group and Meibalance C group. The results are shown in FIGS. 10 and 11.

Figure 13:
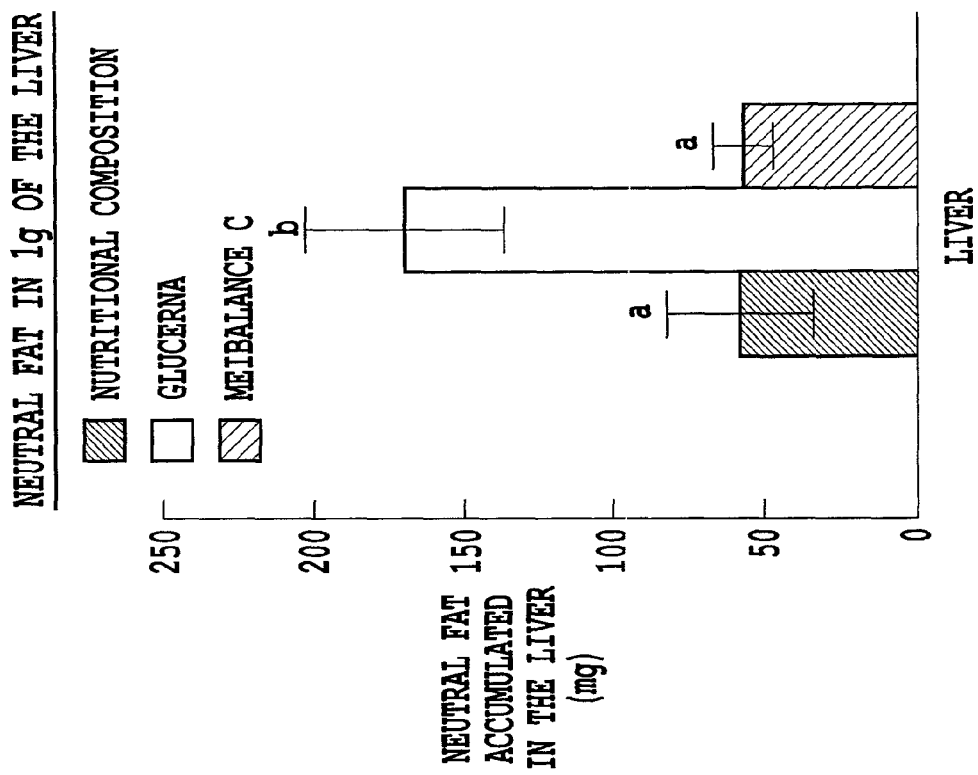
FIG. 13 is a graph showing a neutral fat amount accumulated in liver, per gram of the liver, of mice similar in kind to the above-described mice, after they were fed ad libitum with one of the following: the nutritional composition, Glucerna or Meibalance C powder for 9 weeks. In the diagram, (■) means the nutritional composition, (□) means Glucerna and (♦) means Meibalance C. Each point is a mean value±standard deviation (n=8). *P<0.05: no significant difference when the letter is the same (Mann-Whitney U-test).
Figure 12:
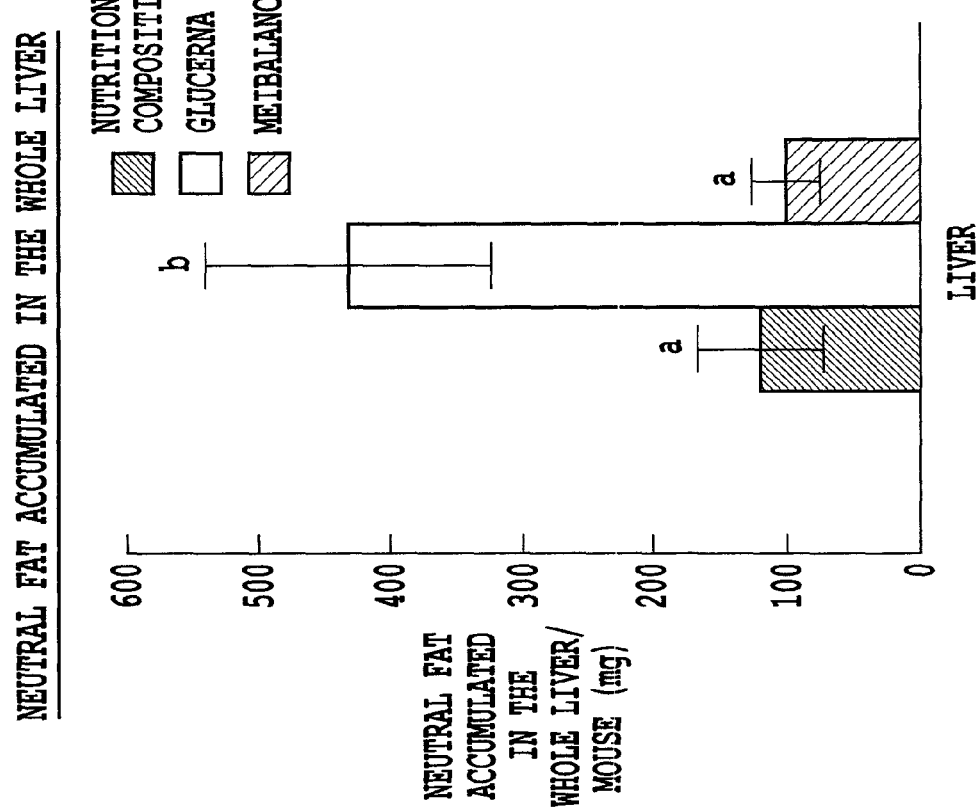
FIG. 12 is a graph showing neutral fat accumulated in the liver, per liver, of mice similar in kind to the above-described mice, after they were fed ad libitum with one of the following: the nutritional composition, Glucerna or Meibalance C powder for 9 weeks. In the diagram, (■) means the nutritional composition, (□) means Glucerna and (♦) means Meibalance C. Each point is a mean±standard deviation (n=8). *P<0.05: no significant difference when the letter is the same (Mann-Whitney U-test).

Even from the macroscopic observation, the liver of the Glucerna intake group changed into a conspicuously fat liver, while no particular change was recognized in the liver of each of the nutritional composition and Meibalance C groups. The neutral fat accumulation amount in the liver and neutral fat amount per g of the liver became markedly high in the Glucerna intake group compared with those in the nutritional composition and Meibalance C intake groups. The results are shown in FIGS. 12 and 13.

C57BL/KSJ-db/db Jcl mice were discovered in 1966 in C57BL/KsJ colonies derived from C57BL/6J mice as mutation type mice which spontaneously display marked diabetic symptoms such as hyperphagia, obesity and hyperinsulinemia. These mice are obese diabetic mice showing type II diabetic morbidity. They start obesity from 4 to 5 weeks old, and with a weight increase, the blood sugar level starts increase from 6 to 7 weeks. The obesity is said to be caused by hyperphagia. They are used widely for analyzing the onset mechanisms of obesity, diabetes and complications thereof, and pharmacological screening of blood sugar level lowering agents.

From the test results using these mice, it has been found that the nutritional composition of the present invention is superior in long-term blood sugar control and lipid metabolism to Glucerna used for nutritional management and blood sugar control of patients suffering from abnormal glucose metabolism. For the prevention of chronic complications of diabetes, it is very important to maintain proper blood sugar levels for long periods. According to reports (N. Eng. J. Med. 329:977-986, 1993; Diabetes Care 20: 621-622, 1997; UKPDS 33. Lancet 352:854-865, 1998), onset and advance of retinopathy or nephropathy can be suppressed if a diabetic patient has HbA1c maintained at 7% or less.

It has also been found that the nutritional composition of the present invention is similar to Glucerna in its effect for improving nutritional management of patients abnormal glucose metabolism.

Test 5 (Visceral Fat Accumulation Suppressive Effect on Normal Mice by Long Term Administration)

As test animals, 4-week-old C57BL/6 Jc 1 mice were purchased (from CLEA JAPAN). They were habituated with an ordinary diet ("CRF=1", trade name; product of Oriental Yeast Industry) for one week and provided for the test as 5-week-old mice. They were weighed and then classified into three groups (n=9) (weight upon classification was regarded as that on Day 0), that is, a group to which a powdery nutritional composition was to be administered, a group to which Glucerna powder was to be administered and a group to which Meibalance C powder was to be administered, so that the weight would be equal among these three groups. After classification, they were fed ad libitum with the nutritional composition prepared in Example 4, Glucerna and Meibalance C instead of the ordinary diet and their weight and intake amount were measured periodically. From the mice fed ad libitum for 1 month, the blood was collected into a heparin-treated tube from their orbit under anesthesia with diethyl ether. After blood collection and celitomy, the liver, kidney, spleen, epididymis fat and posterior peritoneum fat were excised and they were weighed. A portion of the excised liver was homogenized with 0.5% Triton X-100/0.85% NaCl. The supernatant was collected by centrifugal separation (at 10000 rpm, for 10 minutes). The total cholesterol level and neutral fat in the supernatant were measured using Cholesterol E-Test Wako and Triglyceride Test Wako (each, product of Wako Pure Chemicals).

Static analysis of data were all carried out by the Mann-Whitney U test. The results were indicated by mean±standard deviation. Different letters mean a significant difference, while the same letters mean no significant difference.

Figure 15:
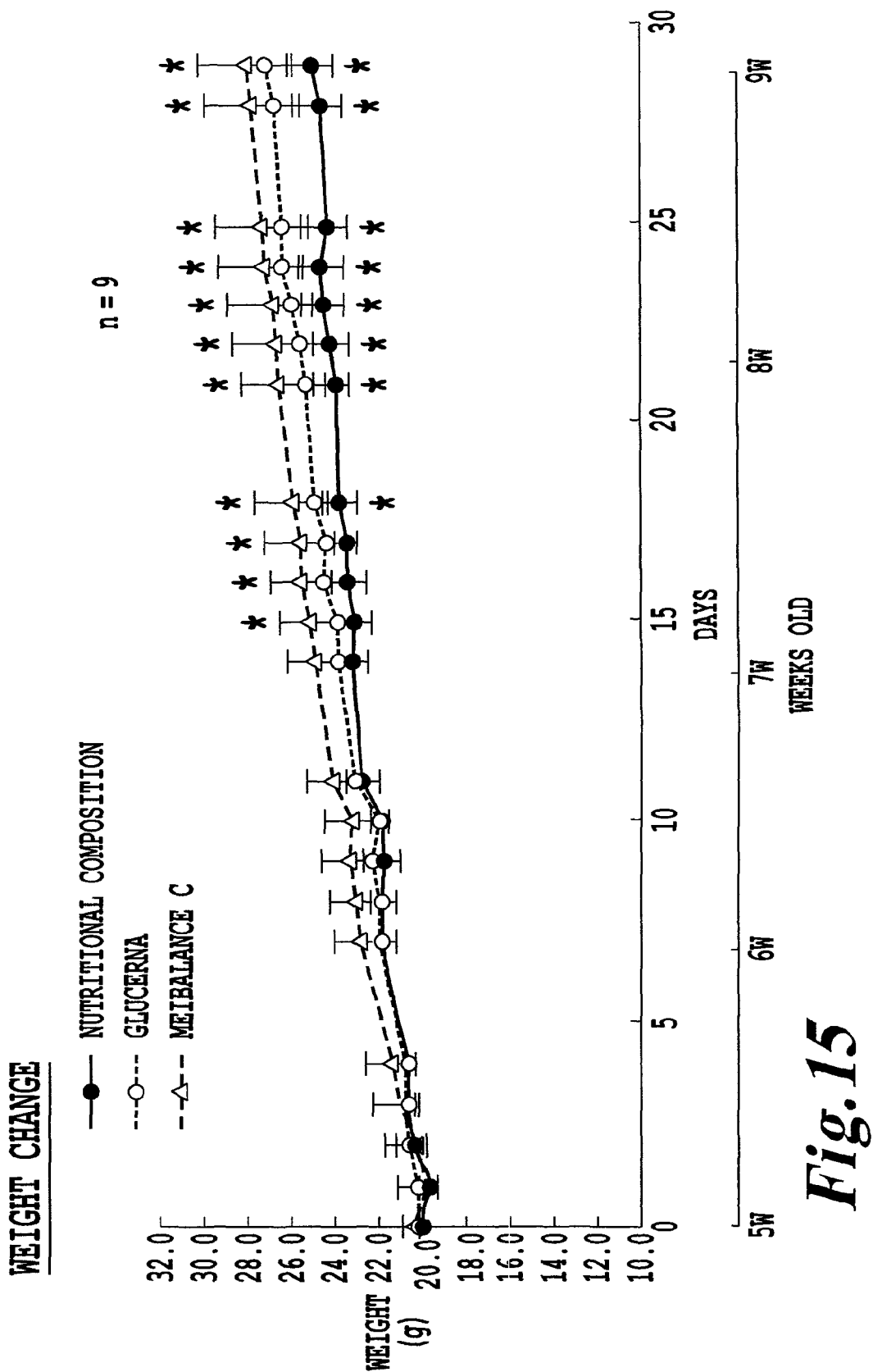
FIG. 15 is a graph showing a change in the weight of mice similar in kind to the above-described ones after they were fed ad libitum with one of the following: nutritional composition, Glucerna or Meibalance C powder for 1 month. In the diagram, (●) means the nutritional composition, (○) means Glucerna and (△) means Meibalance C. Each point is a mean±standard deviation (n=9). *: P<0.05 (Mann-Whitney U-test).

Among the three groups, the nutritional composition, Glucerna and Meibalance C, there exists almost no difference in the change in intake energy (converted from the intake amount) fed ad libitum. With regards to weight change, there exists almost no difference among the groups until their growth period, that is, 5 to 7-weeks old and these groups show a similar weight increase. From the sexual maturation period to the test completion day, more specifically, from 7- to 9-weeks old, the weight increase in the nutritional group was significantly lower than that of the other two groups. The results are shown in FIGS. 14 and 15.

Figures 16, 17:
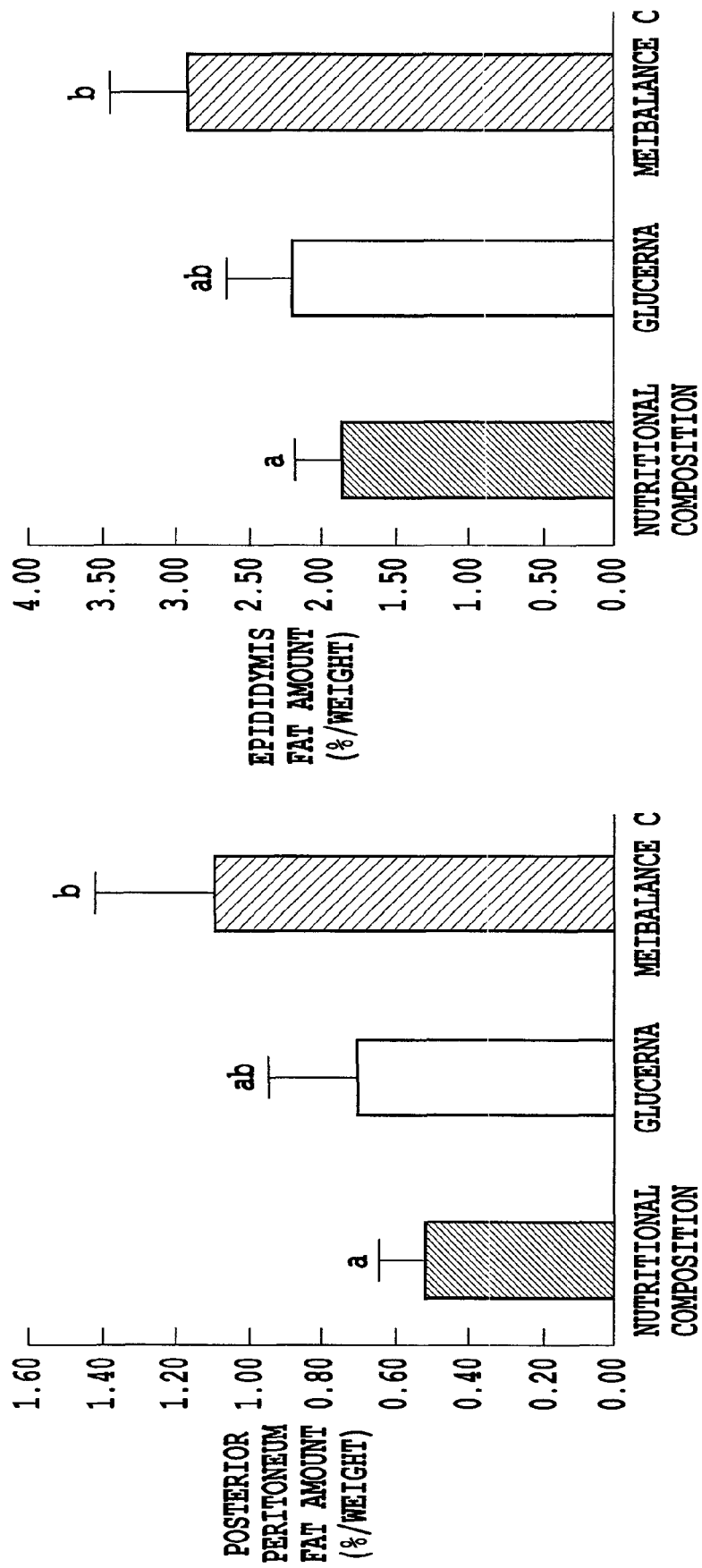
FIG. 16 is a graph showing the posterior peritoneum fat amount (%/weight) of mice similar in kind to the above-described mice after they were fed ad libitum with one of the following: nutritional composition, Glucerna or Meibalance C powder for 9 weeks. In the diagram, (■) means the nutritional composition, (□) means Glucerna and (◆) means Meibalance C. Each point is a mean±standard deviation (n=9). *P<0.05: no significant difference when the letter is the same (Mann-Whitney U-test).
FIG. 17 is a graph showing the epididymis fat amount of mice similar in kind to the above-described mice, after they were fed ad libitum with one of the following: the nutritional composition, Glucerna or Meibalance C powder for 1 month. In the diagram, (■) means the nutritional composition, (□) means Glucerna and (◆) means Meibalance C. Each point is a mean±standard deviation (n=9). *P<0.05: no significant difference when the letter is the same (Mann-Whitney U-test).

As a result of macroscopic observation of anatomy after feeding ad libitum for 1 month, no abnormality was recognized in the organs of each group, but there existed an apparent difference in the amount of visceral fat. Macroscopic observation revealed that the visceral fat amount was greater in the following order: the Meibalance C group, the Glucerna group and the nutrition composition group. With regards to the epididymis fat amount (%/weight) and posterior peritoneum fat amount (%/weight), the nutritional composition group was significantly lower than the Meibalance C group. The results are shown in FIGS. 16 and 17. Comparison with the Glucerna group shows that the nutritional composition group was lower but their difference is not significant. The neutral fat amount per g of the liver was almost the same among the nutritional composition, Glucerna and Meibalance C groups, while the cholesterol level per g of liver was significantly low in the nutritional composition group compared with the Glucerna group and the Meibalance C group.

When the nutritional composition was fed to the mice over a growth period of 2 weeks (from 5 week old to 7 week old), the intake energy and a weight increase were similar to those when Glucerna and Meibalance C groups were fed as control. This suggests that in the growth period, the nutritional composition has similar nutritional effects to Glucerna and Meibalance C. Although there was not a large difference in the intake energy among these three groups from the sexual maturation period after 7 weeks old, the weight of the nutritional composition group showed an increase significantly less than the Glucerna and Meibalance C groups. These results suggest that the nutritional composition has a weight gain suppressing effect for mice prior to the sexual maturation period, compared with Glucerna and Meibalance C groups. Since the amounts of epididymis fat and posterior peritoneum fat, which are main visceral fats, were lower in the nutritional composition group than those in the Glucerna and Meibalance C groups, it has been concluded that in the nutritional composition, suppression of the accumulation of visceral fats results in suppression of a weight increase. The blood sugar level and serum insulin level after intake of the nutritional composition proved to be lower than those of Meibalance C so that it can be called low G.I. (glycemic index) food. The nutritional composition is therefore useful as a food for the prevention of obesity or as a diet food, as well as a food for diabetic patients.

INDUSTRIAL APPLICABILITY

The nutritional composition of the present invention is useful as an oral or tube feeding nutrient, therapeutic diet, diet for diabetic patients at home, obesity preventing diet or food with health claims for nutritional management or blood sugar level control of patients suffering from diabetes or glucose intolerance, or for prevention of obesity. It is useful as a prepared liquid nutritional composition for nutritional management, blood sugar control or obesity prevention of type I or II diabetic patients, or a tube feeding or enteral nutrient for patients suffering from severe cerebral disorders or having trauma to the brain (with hyperglycemia induced by hypermetabolism and hypercatabolism) or aged patients following operation.

The invention claimed is:

1. A nutritional composition which comprises a protein, a lipid and a carbohydrate, wherein energy percentages supplied by the protein, lipid and carbohydrate are 10 to 25%, 20 to 35% and 40 to 60%; respectively; wherein oleic acid is 60 to 90% of the lipid energy percentage and palatinose and/or trehalulose is 60 to 100% of the carbohydrate energy percentage.

2. A nutritional composition of claim 1, wherein the lipid comprises at least one selected from the group consisting of a milk phospholipid, soybean lecithin, high oleic sunflower oil and perilla oil.

3. A blood-sugar-level controlling method, which comprises administering to a patent in need thereof, an effective amount of a nutritional composition comprising a protein, a lipid and a carbohydrate, wherein energy percentages supplied by the protein, lipid and carbohydrate are 10 to 25%, 20 to 35% and 40 to 60%, respectively; wherein oleic acid is 60 to 90% of the lipid energy percentage and palatinose and/or trehalulose is 60 to 100% of the carbohydrate energy percentage.

4. A method according to claim 3, wherein the lipid of the composition comprises at least one selected from the group consisting of a milk phospholipid, soybean lecithin, high oleic sunflower oil and perilla oil.

5. A method according to claim 3, wherein the patient is suffering from diabetes, glucose intolerance, or obesity.

6. A method according to claim 5, wherein the composition is a diet for diabetic patients at home or an obesity treating or reducing diet.

7. A method according to claim 5, wherein the composition is an oral or tube feeding (enteral) nutrient.

8. An obesity treating or reducing method, which comprises administering to a patient in need thereof, an effective amount of a nutritional composition comprising a protein, a lipid and a carbohydrate, wherein energy percentages supplied by the protein, lipid and carbohydrate are 10 to 25%, 20 to 35% and 40 to 60%, respectively; wherein oleic acid is 60 to 90% of the lipid energy percentage and palatinose and/or trehalulose is 60 to 100% of the carbohydrate energy percentage.

9. A method according to claim 8, wherein the lipid of the composition comprises at least one selected from the group consisting of a milk phospholipid, soybean lecithin, high oleic sunflower oil and perilla oil.

10. A method according to claim 8, wherein the composition is an oral or tube feeding (enteral) nutrient.

11. A nutritional composition of claim 1, wherein energy percentages supplied by the protein, lipid and carbohydrate are 10 to 24%, 20 to 30.2% and 40 to 60%; respectively; wherein oleic acid is 60 to 80% of the lipid energy percentage and palatinose and/or trehalulose is 60 to 80% of the carbohydrate energy percentage.

12. A nutritional composition of claim 1, wherein the carbohydrate includes maltodextrin, xylitol, or a mixture thereof.

13. A nutritional composition of claim 1, wherein at least palatinose is present.

14. A nutritional composition of claim 1, wherein at least trehalulose is present.

* * * * *

UNITED STATES PATENT AND TRADEMARK OFFICE
CERTIFICATE OF CORRECTION

| | | |
|---|---|---|
| PATENT NO. | : 7,815,947 B2 | Page 1 of 1 |
| APPLICATION NO. | : 12/275296 | |
| DATED | : October 19, 2010 | |
| INVENTOR(S) | : Kenji Mizumoto et al. | |

It is certified that error appears in the above-identified patent and that said Letters Patent is hereby corrected as shown below:

On the title page, Item (30), the Foreign Application Priority Data is incorrect. Item (30) should read:

-- (30)    Foreign Application Priority Data

Sep. 7, 2001       (JP) ............................ 2001-272463
Mar. 15, 2002      (JP) ............................ 2002-073141
May 31, 2002       (JP) ............................ 2002-160602 --

Signed and Sealed this
Eleventh Day of January, 2011

David J. Kappos
*Director of the United States Patent and Trademark Office*